(12) United States Patent
Besidski et al.

(10) Patent No.: US 7,618,993 B2
(45) Date of Patent: Nov. 17, 2009

(54) COMPOUNDS

(75) Inventors: Yevgeni Besidski, Södertälje (SE); Martin Nylöf, Södertälje (SE); Inger Kers, Södertälje (SE); Karin Skogholm, Södertälje (SE); Shawn Johnstone, Montreal (CA); Paul Jones, Montreal (CA); Denis Labrecque, Montreal (CA); Andrew Griffin, Montreal (CA)

(73) Assignee: AstraZeneca AB, Sodertalje (SE)

( * ) Notice: Subject to any disclaimer, the term of this patent is extended or adjusted under 35 U.S.C. 154(b) by 505 days.

(21) Appl. No.: 11/614,346

(22) Filed: Dec. 21, 2006

(65) Prior Publication Data

US 2008/0171770 A1 Jul. 17, 2008

Related U.S. Application Data

(60) Provisional application No. 60/753,604, filed on Dec. 23, 2005.

(51) Int. Cl.
*A61K 31/4184* (2006.01)
*C07D 235/04* (2006.01)

(52) U.S. Cl. .................. 514/394; 548/301.7; 548/302.7; 548/304.4; 548/309.7; 514/385; 514/393

(58) Field of Classification Search ............. 548/301.7, 548/302.7, 304.4, 309.7; 514/385, 393, 394
See application file for complete search history.

(56) References Cited

U.S. PATENT DOCUMENTS

| | | | |
|---|---|---|---|
| 3,624,103 | A | 11/1971 | De Martiis et al. |
| 3,839,347 | A | 10/1974 | Fisher et al. |
| 4,722,929 | A | 2/1988 | Austel et al. |
| 4,738,981 | A | 4/1988 | Horwell |
| 6,794,404 | B2 | 9/2004 | Beaulieu et al. |
| 2003/0149050 | A1 | 8/2003 | Jagtap et al. |
| 2003/0158188 | A1 | 8/2003 | Lee et al. |
| 2004/0092569 | A1 | 5/2004 | Demaine et al. |
| 2004/0152690 | A1 | 8/2004 | Balan et al. |
| 2004/0248983 | A1 | 12/2004 | Morie et al. |
| 2006/0205802 | A1 | 9/2006 | Liu et al. |
| 2006/0287377 | A1 | 12/2006 | Besidski et al. |
| 2007/0066586 | A1 | 3/2007 | Tokumasu et al. |
| 2008/0015222 | A1 | 1/2008 | Besidski et al. |

FOREIGN PATENT DOCUMENTS

| | | |
|---|---|---|
| DE | 2300521 | 7/1973 |
| EP | 0149200 | 12/1984 |
| EP | 0419210 | 3/1991 |
| EP | 1312601 A1 | 5/2003 |
| EP | 0882718 B1 | 8/2005 |
| GB | 1186504 | 4/1970 |
| WO | 94/22859 A1 | 10/1994 |
| WO | 99/00115 A1 | 1/1999 |
| WO | 01/12189 A1 | 2/2001 |
| WO | 01/85722 A1 | 11/2001 |
| WO | 01/96336 A2 | 12/2001 |
| WO | 02/50031 A1 | 6/2002 |
| WO | 02/072536 A1 | 9/2002 |
| WO | 02/085866 A1 | 10/2002 |
| WO | 02/090326 A1 | 11/2002 |
| WO | 02/100819 A1 | 12/2002 |
| WO | 02/100822 | 12/2002 |
| WO | 03/014064 A1 | 2/2003 |
| WO | 03/022809 A2 | 3/2003 |
| WO | 03/027076 A2 | 4/2003 |
| WO | 03/049702 A2 | 6/2003 |
| WO | 03/053945 A2 | 7/2003 |
| WO | 03/068749 A1 | 8/2003 |
| WO | 2004/000828 A1 | 12/2003 |
| WO | 2004/024154 A1 | 3/2004 |
| WO | 2004/024710 A1 | 3/2004 |
| WO | 2004100865 A2 | 11/2004 |
| WO | 2004108712 A1 | 12/2004 |
| WO | 2005021539 A1 | 3/2005 |
| WO | 2005095327 A1 | 10/2005 |
| WO | 2006033620 A1 | 3/2006 |
| WO | 2008/018827 A1 | 2/2008 |

OTHER PUBLICATIONS

Gallard, et at., Journal of Enzyme Inhibition and Medicinal Chemistry, vol. 18, No. 2. 2003,""New N-Pyridinyl (methyl)-N1-Substituted . . . Systemic anti-Inflammatory Agents"", pp. 201-208.
T.L. Gilchrist, "Heterocyclic Chemistry", 2nd Edition, Longman Scientific andTechnical (1992), pp. 248-282.
Hwang, et al., "Hot Channels in Airways : Pharmacology of the Vanilloid Receptor"; Respiratory, Curr Opin Pharmacol 2002, June, 2(3) pp. 235-242.
Rashid, et al ., "Novel Expression of Vanilloid . . . in Neuropathic Pain"; J. Pharmacology & Experimental Therapeutics, vol. 304, No. 3, pp. 940-948, 2003.
Szallasi, et al . "Vanilloid (Capsaicin) Receptors in Health and Disease"; Am J Clin Pathot 2002, 118:110-121.
Tominaga, et al., "The Cloned Capsaicin Receptor Integrates Multiple Pain-Producing Stimuli" ; Neuron, 21:531-543 (1998).

(Continued)

*Primary Examiner*—Golam M Shameem
(74) *Attorney, Agent, or Firm*—Karen H. Kondrad

(57) ABSTRACT

The present invention relates to new compounds

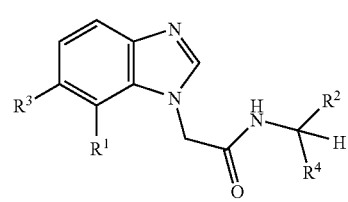

(I)

or salts, solvates or solvated salts thereof, processes for their preparation and to new intermediates used in the preparation thereof, pharmaceutical compositions containing said compounds and to the use of said compounds in therapy.

10 Claims, No Drawings

OTHER PUBLICATIONS

Walker, et al., "The VRI Antagonist Capsazepine Reverses Mechanical Hyperalgesia in Models of Inflammatory and Neuropathic Pain"; J. Pharmacology & Experimental Therapeutics, vol. 304:56-62 (2003).

Yiangou, et al., "Capsaicin Receptor VRI and ATP-Gated ion Channel P2X3, in Human Urinary Bladder"; BJU International (2001), 87, pp. 774-779.

Non-final Office Action mailed on Jan. 7, 2008, for U.S. Appl. No. 10/556,229, AstraZeneca.

Non-final office Action mailed on Jul. 16, 2007, for U.S. Appl. No. 10/556,229, AstraZeneca.

Co-pending U.S. Appl. No. 11/836,221, filed Aug. 9, 2007.

Non-final Office Action mailed on May 16, 2008, for U.S. Appl. No. 10/557,806, AstraZeneca.

Non-final Office Action mailed on Jul. 23, 2008 for U.S. Appl. No. 10/557,806, AstraZeneca.

Beilstein Institute for Organic Chemistry, Frankfurt-Main, Germany; XP002291482, BRN 838602 abstract and Kamel et al, J. Prakt. Chem., vol. 31, 1966, pp. 100-105.

Beilstein Institute for Organic Chemistry, Frankfurt-Main, Germany; XP002291483 BRN 926470 abstract and Osman: Kolor. ERT., vol. 11, 1969, p. 118.

Beilstein Institute for Organic Chemistry, Frankfurt-Main, Germany; XP002291484 BRN 311062 abstract & Pinnow; Wiskott: Chem. Ber., vol. 32, 1899, p. 900.

Beilstein Institute for Organic Chemistry, Frankfurt-Main, Germany; XP002291485 BRN 189489 abstract & Foster: J. Chem. Soc., 1957, pp. 4687-4688.

Beilstein Institute for Organic Chemistry, Frankfurt-Main, Germany; XP002291490 BRN 326965 abstract & V. Walter; Kessler: J. Prak. Chem., vol. 2, No. 74, 1906, p. 198.

Kumar, et al., "Cyanoethylation of Benzimidazoles: Synthesis & Biological Activities of Some New 1-(beta-Cyanoethyl)benzimidazoles & Their Derivatives", Indian Journal of Chemistry, Oct. 1985, vol. 24B, p. 1098-1101.

Lindberg, et al., "Long-Time Persistence of Superantigen-Producing *Staphylococcus aureus* Strains in the Intestinal Microflora of Healthy Infants", Pediatric Research 48:741-747 (2000).

McDonnell, et al., 7-Hydroxynaphthalen-l-yt-Urea and -Amide Antagonists of Human Vanilloid Receptor 1; Bioorganic & Medicinal Chemistry Letters 14 (2004), pp. 531-534.

Musso, et al., "Indanylidenes . 1 . Design and Synthesis of (E)-2-(4,6-Difluoro-1-indanylidene)acetamide, a Potent, Centrally Acting Muscle Relaxant with Antiinflammatory and Analgesic Activity"; J. Med. Client 2003, 46, pp. 399-408.

Patent Abstracts of Japan vol. 2000, No. 07, Sep. 29, 2000 & JP 2000 095767 A (Takeda Chem Ind Ltd), 4 Pril 2000.

Rudin, et al., "Staphylococcal Enterotoxin B and High Dose Phytohemagglutinin Induce a Th1- Skewed Response in Neonates Irrespective of Atopic Status at 2 Years of Age", Scandinavian Journal of Immunology 52:415-461 (2000).

Sasaki, et al., "Prevention of collagen-induced arthritis with the superantigen Staphylococcal enterotoxin B", Patho-physiology 4:25-31 (1997).

Soos, et al., "Treatment PL/J mice with the superantingen, staphylococcal enterotoxin B, prevents development of experimental allergic encephalomyelitis", J Neuroimmunology 43:39-44 (1993).

Willitzer, H. et al., "Synthese und antivirale Wirsamkeit von substituierten 5-Ureido- und 5- Thioureidobenzimidazolderivaten" Pharmazie, VEB VERLAG VOLK und Gesundheit. Berlin, Germany vol. 33, No. 1, Jan. 1978 (1078-01), pp. 30-38, XP002209435 ISSN: 0031-7144 English Abstract is cited as access. No. 1978:424221.

STN International, File CAPLUS, accession No. 1978:424221, document No. 89:24221, Willitzer et al., "Synthesis and antiviral activity of substituted 5-ureido- and 5-thioureidobenzimidazole derivatives", & Pharmazie (1978), 33(1) 30-8.

STN Intl. File CAPLUS, accession No. 1958:50566, doc No. 52-50566, Foster, R. "1-Ethyl-2-methyl-5-nitrobenzimidazole" & Journal of the Chem. Society, Abstracts (1957) 4687-8.

STN International, file CHEMCATS, Accession No. 2000:912544, Apr. 24, 2003, CHS 0297096, 1H-Benzimidazole-1-acetamide, N-[3-(trifluoromethyl)phenyl]-CAS Registry No. 294669-15-1.

STN International, file CHEMCATS, Accession No. 2000:532079, Apr. 23, 2003, BAS 0238979,1H-Benzimidazole-1-acetamide, N-(3-chlorophenyl)-CAS Registry No. 116488-26-7.

STN International, file CHEMCATS, Accession No. 2001:10738, Apr. 24, 2003, NS11937, 1H-Indole-3-butanamide, N-(4-methylphenyl)-CAS Registry No. 313550-48-0.

STN International, file CHEMCATS, Accession No. 2001:1505160, Apr. 29, 2003, AG-690/40696518,1H-Benzimidazole-l-acetamide, N-(2,3-dichlorophenyl)-, CAS Registry No. 332384-60-8.

STN International, file CHEMCATS, Accession No. 2002:2035573, Jul. 9, 2002, ASN 1816063,1H-Benzimidazole-l-acetamide, N-(3-chloro-4-methylphenyl)—CAS Registry No. 332908-87-9.

STN International, file CHEMCATS, Accession No. 2002:2042451, Jul. 9, 2002, ASN 4428244,1H-Benzimidazole-l-acetamide,N-(5-amnino-2-methylphenyl)—CAS registry No. 436095-70-4.

STN International, file CHEMCATS, Accession No. 2003 :454497, Apr. 30, 2003, ASN 5212034,1H-Indole-3-acetamide, N-[4-(1-methylethyl)phenyl]—CAS Registry No. 460336-68-9.

STN International, file CHEMCATS, Accession No. 2003:454500, Apr. 30, 2003, ASN 5212038,1H-Indole-3-acetamide, N-(3,5-dimethoxyphenyl)—CAS Registry No. 460336-71-4.

STN International, file CHEMCATS, Accession No. 2003 :1778448, Jul. 9, 2002 . ASN 3067491,1H-Benzimidazole-l-acetamide, N-(2-flurophenyl)—CAS Registry No. 483326-88-1.

STN International, file CHEMCATS, Accession No. 2003:1780032 . Jul. 9, 2002, ASN 3110045, 1H-Benzimidazole-l-acetamide, 5,6-dimethyl-N-[2-(trifluoromethyl) phenyl]- CAS Registry No. 483347-09-7.

STN International, file CHEMCATS, Accession No. 2003:1780036, Jul. 9, 2002, ASN 3110053,1H-Benzimidazole-1-acetamide, N-(2,4-dimethoxyphenyl)-5,6-dimethyl- CAS Registry No. 483347-12-2.

STN International,file CHEMCATS, Accession No. 2003 :1780041 . Jul. 9, 2002, ASN 3110088,1H-Benzimidazole-1-acetamide, N-[4-(dimethylamino)phenyl]-5,6-dimethyl- CAS Registry No. 483347-17-7.

STN International, file CHEMCATS, Accession No. 2003 :1783073, Jul. 9, 2002, ASN 3212475, 1H-Benzimidazole-1-acetamide, N-(3-fluorophenyl)- CAS Registry No. 483978-05-8.

STN International, file CHEMCATS, Accession No. 2003:2842871, Apr. 30, 2003, BAS 5595011, 1H-Indole-3-acetamide, N-(3-fluoro-4-methylphenyl)—CAS Registry No. 510764-85-9.

STN International, file CHEMCATS, Accession No. 2003:3562090, Apr. 30, 2003, ZT-5586656, 1H-Indole-3-propanamide, N-[2-(1-methylethyl)phenyl]—CAS Registry No. 556791-23-2.

STN International, file CHEMCATS, Accession No. 2003 :3425665, Apr. 30, 2003, ZT-2132403, 1H-Indole-3-propanamide,N-[4-(1,1-dimethylethyl)phenyl]—CAS Registry No. 562052-38-4.

STN International, file CHEMCATS, Accession No. 2003:3428083, Apr. 30, 2003, ZT-2150185, 1H-Indole-3- propanamide,N-(2-chloro-4-methylphenyl)-,CAS Registry No. 562794-00-7.

STN International, file HCAPLUS, Accession No. 2002:737351. document No. 138:265138, Olgen, Sureyya et al, Synthesisand antioxidant properties of Novel N-substituted indole-2-carboxamide and indole-3-acetamide derivatives, & Archiv der Pharmazie (Weinheim, Germany) (2002), 335(7), 331-338.

STN International, Accession No. 2002 :695939 document No. 137 : 232452, Rotta Research Laboratorium S.p. A ..,"Preparation of benzamidines having antiinfammatory & immunosuppressive activity", & W02002070468, A2, 20020912.

STN International, File HCAPLUS, accession No. 2000:214835, document No. 132:265201, Takeda Chemical Industries Ltd., "Preparation of imidazole derivatives as gonadotropin-releasing hormone antagonists", & JP A2,200095767, 20000404.

STN International, file HCAPLUS, Accession No. 2000:825244, document No. 134:147129, Jamieson, Craig, et al., "A rapid approach for the optimization of polymer supported reagents in synthesis", & Synlett (2000), (11), 1603-1607.

STN International, file HCAPLUS, Accession No. 1988:610992, document No. 109:210992, Shah, V.H. et al, "Studies on acetamide derivatives, Part-II. Preparation, antimicrobial and anthelmintic activity of N-arylaminoacetyl-benzimidazole/ sulfadiazine or sulfamethazine and N-arylbenzimidazol-1-yl/sulfadiazin-4-yl or sulfamethazin-4-yl/ acetamides", & Journal of the Indian ChemicalSociety (1987), 64(11), 678-81.

STN International, file HCAPLUS, Accession No. 1958:31856 document No. 52:31856, Cacace, Fulvio, et al.,"Benzimidazole-N-acetic acid and its growth activity", & Atti accad. nazl. Lincei. Rend., Classe sci. fiz., mat. e nat (1957), 22, 510-13.

STN International, file HCAPLUS, Accession No. 1993:102385, document No. 118:102385, Gallant, Michel et al., "A stereoselective synthesis of Indole-Beta-N-glycosides: an application to the synthesis of rebeccamycin", & Jr of Organic Chemistry (1993), 58(2), 343-9.

STN International, file HCAPLUS, Accession No. 1998:227318, document No. 128:308402, Sanwa Kagaku Kenkyusho Co., Ltd., "Preparation of N-(diisopropylphenyl)quinolineacetamides as antiarterioscleroties", & JP, A2, 10095766, 19980414.

STN International, file HCAPLUS, Accession No. 1995:594439, document No. 123:9266, Interneuron Pharm, Inc., "Substituted tryptamines, phenalkylamines and related compounds", & US, A, 5403851,19950404.

STN International CAPLUS acess No. 1967:46373, doc No. 66:26373, Takahashi, S. et al., "Benzimidazole N-oxides . . . Reactivity . . . 3 oxide" & Chem & Pharm Bulletin (1966), 14(11), 1219-27.

STN Intl. File CAPLUS, access No. 1969:492626, doc No. 71:92626, Osman, M.A. "Benzimidazole derivatives . . . and coupling components", & K. Ertesito (1969) 11(5-6), 118-21.

STN International CAPLUS, access No. 1966:51996.

STN International, File Registry, see RN 743444-08-8, Sep. 13, 2004.

Caterina, et al ., "The Capsaicin Receptor : A Heat-Activated Ion Channel in the Pain Pathway"; Nature, vol. 389, Oct. 23, 1997, pp. 816-824.

Collins et al., "Mucosal Tolerance to a Bacterial Superantigen Indicates a Novel AJ Toxic Shock", Infection and Immunity 70:2282-2287 (2002).

COMPOUNDS

The present application claims the priority of U.S. Application Ser. No. 60/753,604 filed on Dec. 23, 2005.

FIELD OF THE INVENTION

The present invention relates to new compounds, to pharmaceutical compositions containing said compounds and to the use of said compounds in therapy. The present invention further relates to processes for the preparation of said compounds and to new intermediates used in the preparation thereof.

BACKGROUND OF THE INVENTION

Pain sensation in mammals is due to the activation of the peripheral terminals of a specialized population of sensory neurons known as nociceptors. Capsaicin, the active ingredient in hot peppers, produces sustained activation of nociceptors and also produces a dose-dependent pain sensation in humans. Cloning of the vanilloid receptor 1 (VR1 or TRPV1) demonstrated that VR1 is the molecular target for capsaicin and its analogues (Caterina, M. J., Schumacher, M. A., et. al. Nature (1997) v. 389 p 816-824). Functional studies using VR1 indicate that it is also activated by noxious heat, tissue acidification and other inflammatory mediators (Tominaga, M., Caterina, M. J. et. al. Neuron (1998) v.21, p. 531-543). Expression of VR1 is also regulated after peripheral nerve damage of the type that leads to neuropathic pain. These properties of VR1 make it a highly relevant target for pain and for diseases involving inflammation. While agonists of the VR1 receptor can act as analgesics through nociceptor destruction, the use of agonists, such as capsaicin and its analogues, is limited due to their pungency, neurotoxicity and induction of hypothermia. Instead, agents that block the activity of VR1 should prove more useful. Antagonists would maintain the analgesic properties, but avoid pungency and neurotoxicity side effects. Compounds with VR1 inhibitor activity are believed to be of potential use for the treatment and/or prophylaxis of disorders such as pain, especially that of inflammatory or traumatic origin such as arthritis, ischaemia, cancer, fibromyalgia, low back pain and post-operative pain (Walker et al J Pharmacol Exp Ther. (2003) Jan;304(1):56-62). In addition to this visceral pains such as chronic pelvic pain, cystitis, irritable bowel syndrome (IBS), pancreatitis and the like, as well as neuropathic pain such as sciatia, diabetic neuropathy, HIV neuropathy, multiple sclerosis, and the like (Walker et al ibid, Rashid et al J Pharmacol Exp Ther. (2003) Mar;304(3):940-8), are potential pain states that could be treated with VR1 inhibition. These compounds are also believed to be potentially useful for inflammatory disorders like asthma, cough, inflammatory bowel disease (IBD) (Hwang and Oh Curr Opin Pharmacol (2002) Jun;2(3): 235-42). Compounds with VR1 blocker activity are also useful for itch and skin diseases like psoriasis and for gastroesophageal reflux disease (GERD), emesis, cancer, urinary incontinence and hyperactive bladder (Yiangou et al BJU Int (2001) Jun;87(9):774-9, Szallasi Am J Clin Pathol (2002) 118: 110-21). VR1 inhibitors are also of potential use for the treatment and/or prophylaxis of the effects of exposure to VR1 activators like capsaicin or tear gas, acids or heat (Szallasi ibid).

A further portential use relates to the treatment of tolerance to VR1 activators.

VR1 inhibitors may also be useful in the treatment of interstitial cystitis and pain related to interstitial cystitis.

VR1 inhibitors may also be useful in the treatment of obesity and migraine; WO2006/007851 discloses the use of VR1 antagonists for the treatment of obesity. WO2004/100865 discloses compounds exhibiting inhibitory activity at the vanilloid receptor 1 (VR1).

DETAILED DESCRIPTION OF THE INVENTION

The object of the present invention is to provide compounds of said kind of compounds exhibiting inhibitory activity at the vanilloid receptor 1 (VR1), which compounds exhibit not only improved potency but optimized combinations of potency and other desirable properties, in particular solubility, along with good Drug Metabolism and Pharmacokinetics (DMPK) properties.

The present invention provides compounds of formula I

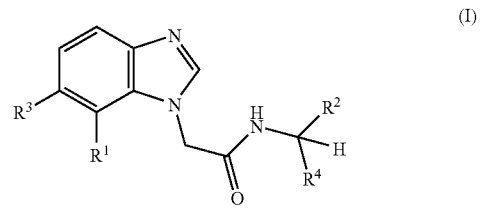

(I)

wherein:
$R^1$ is selected from nitro, cyano, halo, and acetyl; $R^2$ is selected from phenyl, heteroaryl, phenylmethyl, and phenyloxymethyl;
where $R^2$ is optionally substituted with one or more substituents Q selected from $C_{1-6}$alkyl, $C_{1-6}$alkoxy, $C_{1-6}$haloalkyl, halo, $C_{1-6}$haloalkoxy, $C_{3-7}$cycloalkoxy, $C_{3-7}$cycloalkyl, $C_{1-6}$alkynyl, $C_{3-7}$cycloalkylalkoxy, $C_{3-7}$heterocycloalkyloxy, and $C_{1-3}$alkoxyC$_{1-6}$alkoxy, said substituent(s) Q being attached to the aromatic and/or heteroaromatic ring(s) of $R^2$;
$R^3$ is H or F;
$R^4$ is methyl, methoxycarbonyl or ethyl; or $R^2$ and $R^4$ may together form a monocyclic or bicyclic ring system;

and salts, solvates or solvated salts thereof.

One embodiment of the invention relates to compounds of formula I wherein $R^1$ is selected from nitro, cyano, fluoro, chloro, and acetyl.

Another embodiment of the invention relates to compounds of formula I wherein $R^1$ is nitro.

A further embodiment of the invention relates to compounds of formula I wherein $R^1$ is cyano or halo.

One embodiment of the invention relates to compounds of formula I wherein $R^1$ is cyano, chloro, or fluoro.

Another embodiment of the invention relates to compounds of formula I wherein $R^2$ is selected from phenyl, pyridinyl, thienyl, phenylmethyl, and phenyloxymethyl.

A further embodiment of the invention relates to compounds of formula I wherein $R^2$ is phenyl substituted with one or more substituent(s) Q with one substituent Q in para-position relative to the point of attachment.

One embodiment of the invention relates to compounds of formula I wherein $R^2$ is pyridin-3-yl substituted with one or more substituent(s) Q, wherein one substituent Q is a substituent at position 6 of the pyridine ring.

Another embodiment of the invention relates to compounds of formula I wherein $R^2$ is pyridin-2-yl substituted with one or more substituent(s) Q, wherein one substituent Q is a substituent at position 5 of the pyridine ring.

A further embodiment of the invention relates to compounds of formula I wherein $R^2$ is thien-2-yl substituted with one or more substituent(s) Q, wherein one substituent Q is a substituent at position 5 of the thiophene ring.

One embodiment of the invention relates to compounds of formula I wherein $R^2$ is phenylmethyl.

Another embodiment of the invention relates to compounds of formula I wherein $R^2$ is phenoxymethyl.

A further embodiment of the invention relates to compounds of formula I wherein Q is selected from (1-methylprop-2-yn-1-yl)oxy, 1-methylpropyloxy, 2,2,2-trifluoroethoxy, 2,2,3,3-tetrafluoro-propoxy, 2,2-difluoro-ethoxy, 2-fluoro-1-fluoromethyl-ethoxy, 2-fluoroethoxy, 2-methoxy-1-methyl-ethoxy, 2-methoxy-propoxy, chloro, chloro(difluoro)methyl, cyclopentyloxy, cyclopropyl, cyclopropylmethoxy, ethoxy, ethynylphenyl, fluoro, isopropoxy, isopropyl, methoxy, methylpiperidinylox, propoxy, tert-butyl, trifluoromethoxy, and trifluoromethyl.

One embodiment of the invention relates to compounds of formula I wherein $R^2$ is substituted with two substituents Q, one of which is selected from 2-fluoro-1-fluoromethylethoxy, 2-fluoroethoxy, cyclopentyloxy, methoxy, 2-fluoro-1-fluoromethyl-ethoxy, 2-methoxypropyloxy, and methylpiperidinyloxy; and the other one of which is selected from chloro, fluoro, and trifluoromethyl.

Another embodiment of the invention relates to compounds of formula I wherein $R^4$ is methyl.

A further embodiment of the invention relates to compounds of formula I wherein $R^2$ and $R^4$ together form a monocyclic or bicyclic ring system.

One embodiment of the invention relates to compounds of formula I wherein $R^2$ and $R^4$ together form a bicyclic ring system.

Another embodiment of the invention relates to compounds of formula I wherein $R^2$ and $R^4$ together form a chromanyl group.

A further embodiment of the invention relates to compounds of formula I wherein
$R^1$ is selected from nitro, cyano, chloro, fluoro, and acetyl; and
$R^2$ is phenyl substituted with one or more substituent(s) Q selected from (1-methylprop-2-yn-1-yl)oxy, 1-methylpropyloxy, 2,2,2-trifluoro-ethoxy, 2,2,3,3-tetrafluoro-propoxy, 2,2-difluoroethoxy, 2-fluoro-1-fluoromethyl-ethoxy, 2-fluoroethoxy, 2-methoxy-1-methyl-ethoxy, 2-methoxypropoxy, chloro, chloro(difluoro)methyl, cyclopentyloxy, cyclopropyl, ethoxy, ethynylphenyl, fluoro, isopropyl, methylpiperidinyloxy, propoxy, tert-butyl, trifluoromethoxy, and trifluoromethyl, with one substituent Q in para-position relative to the point of attachment. Specifically, $R^1$ may be selected from nitro, cyano, and fluoro; and $R^2$ phenyl may be substituted with one or more substituent(s) Q selected from (1-methylprop-2-yn-1-yl)oxy, 1-methylpropyloxy, 2,2,2-trifluoro-ethoxy, 2,2,3,3-tetrafluoro-propoxy, 2-fluoroethoxy, 2-methoxy-1-methyl-ethoxy, chloro, cyclopentyloxy, cyclopropyl, ethoxy, ethynylphenyl, fluoro, isopropyl, methylpiperidinyloxy, propoxy, tert-butyl, trifluoromethoxy, and trifluoromethyl, with one substituent Q in para-position relative to the point of attachment.

One embodiment of the invention relates to compounds of formula I wherein
$R^1$ is selected from nitro, cyano, chloro, and fluoro; and
$R^2$ is pyridinyl or thienyl substituted with one or more substituent(s) Q selected from 2,2,2-trifluoro-ethoxy, 2,2,3,3-tetrafluoro-propoxy, 2,2-difluoro-ethoxy, 2-fluoro-1-fluoromethyl-ethoxy, 2-fluoroethoxy, 2-isopropoxy, chloro, cyclopentyloxy, cyclopropylmethoxy, isopropoxy, tert-butyl, and trifluoromethyl. Specifically, $R^2$ may be pyridinyl or thienyl substituted with one or more substituent(s) Q selected from 2,2,2-trifluoro-ethoxy, 2,2,3,3-tetrafluoro-propoxy, 2,2-difluoro-ethoxy, 2-isopropoxy, chloro, cyclopentyloxy, cyclopropylmethoxy, isopropoxy, tert-butyl, and trifluoromethyl.

A further embodiment of the invention relates to compounds selected from the group consisting of
2-(6,7-difluoro-1H-benzimidazol-1-yl)-N-{1-[4-(trifluoromethyl)phenyl]ethyl}acetamide,
2-(7-acetyl-1H-benzimidazol-1-yl)-N-(1-{4-[2-fluoro-1-(fluoromethyl)ethoxy]phenyl}ethyl)acetamide,
2-(7-chloro-1H-benzimidazol-1-yl)-N-(1-{4-[2-fluoro-1-(fluoromethyl)ethoxy]phenyl}ethyl)acetamide,
2-(7-chloro-1H-benzimidazol-1-yl)-N-(1-{4-[chloro(difluoro)methyl]phenyl}ethyl)acetamide,
2-(7-chloro-1H-benzimidazol-1-yl)-N-[1-(4-ethynylphenyl)ethyl]acetamide,
2-(7-chloro-1H-benzimidazol-1-yl)-N-{1-[3-chloro-5-(trifluoromethyl)pyridin-2-yl]ethyl}acetamide,
2-(7-chloro-1H-benzimidazol-1-yl)-N-{1-[4-(1,1,2,2-tetrafluoroethoxy)phenyl]ethyl}acetamide,
2-(7-chloro-1H-benzimidazol-1-yl)-N-{1-[4-(2,2-difluoroethoxy)phenyl]ethyl}acetamide,
2-(7-chloro-1H-benzimidazol-1-yl)-N-{1-[4-(trifluoromethyl)phenyl]ethyl}acetamide,
2-(7-chloro-1H-benzimidazol-1-yl)-N-{1-[6-(2,2,2-trifluoroethoxy)pyridin-3-yl]ethyl}acetamide,
2-(7-chloro-1H-benzimidazol-1-yl)-N-{1-[6-(2,2,3,3-tetrafluoropropoxy)pyridin-3-yl]ethyl}acetamide,
2-(7-Chloro-benzoimidazol-1-yl)-N-[1-(6-isopropoxy-pyridin-3-yl)-ethyl]-acetamide,
2-(7-cyano-1H-benzimidazol-1-yl)-N-(1-{4-[2-fluoro-1-(fluoromethyl)ethoxy]phenyl}ethyl)acetamide,
2-(7-cyano-1H-benzimidazol-1-yl)-N-[1-(4-isopropylphenyl)ethyl]acetamide,
2-(7-cyano-1H-benzimidazol-1-yl)-N-{1-[3-fluoro-4-(trifluoromethyl)phenyl]ethyl}acetamide,
2-(7-cyano-1H-benzimidazol-1-yl)-N-{1-[4-(2,2,2-trifluoroethoxy)phenyl]ethyl}acetamide,
2-(7-cyano-1H-benzimidazol-1-yl)-N-{1-[4-(trifluoromethoxy)phenyl]ethyl}acetamide,
2-(7-cyano-1H-benzimidazol-1-yl)-N-{1-[4-(trifluoromethyl)phenyl]ethyl}acetamide,
2-(7-cyano-1H-benzimidazol-1-yl)-N-{(1S)-1-[4-(trifluoromethyl)phenyl]ethyl}acetamide,
2-(7-cyano-1H-benzimidazol-1-yl)-N-{1-[4-[2-fluoro-1-(fluoromethyl)ethoxy]-2-(trifluoromethyl)phenyl]ethyl}acetamide,
2-(7-fluoro-1H-benzimidazol-1-yl)-N-[1-(4-isopropylphenyl)ethyl]acetamide,
2-(7-fluoro-1H-benzimidazol-1-yl)-N-{1-[4-(trifluoromethyl)phenyl]ethyl}acetamide,
2-(7-nitro-1H-benzimidazol-1-yl)-N-{1-[4-(1,1,2,2-tetrafluoroethoxy)phenyl]ethyl}acetamide,
2-(7-nitro-1H-benzimidazol-1-yl)-N-{1-[4-(2,2,2-trifluoroethoxy)phenyl]ethyl}acetamide,
2-(7-nitro-1H-benzimidazol-1-yl)-N-{1-[4-(trifluoromethoxy)phenyl]ethyl}acetamide,
2-(7-nitro-1H-benzimidazol-1-yl)-N-{1-[4-(trifluoromethyl)phenyl]ethyl}acetamide,
2-(7-nitro-1H-benzimidazol-1-yl)-N-{1-[5-(trifluoromethyl)pyridin-2-yl]propyl}acetamide,
2-(7-nitro-1H-benzimidazol-1-yl)-N-{1-[5-(trifluoromethyl)pyridin-2-yl]ethyl}acetamide, 2-(7-nitro-1H-benzimidazol-1-yl)-N-{1-[6-(2,2,2-trifluoroethoxy)pyridin-3-yl]ethyl}acetamide,
2-(7-nitro-1H-benzimidazol-1-yl)-N-{1-[6-(2,2,3,3-tetrafluoropropoxy)pyridin-3-yl]ethyl}acetamide,
methyl(4-tert-butylphenyl){[(6,7-difluoro-1H-benzimidazol-1-yl)acetyl]amino}acetate,
N-((1S)-1-{4-[(1-methylprop-2-yn-1-yl)oxy]phenyl}ethyl)-2-(7-nitro-1H-benzimidazol-1-yl)acetamide,
N-((1S)-1-{4-[2-fluoro-1-(fluoromethyl)ethoxy]phenyl}ethyl)-2-(7-nitro-1H-benzimidazol-1-yl)acetamide,
N-(1-{2-chloro-4-[2-fluoro-1-(fluoromethyl)ethoxy]phenyl}ethyl)-2-(7-cyano-1H-benzimidazol-1-yl)acetamide,
N-(1-{4-[chloro(difluoro)methyl]phenyl}ethyl)-2-(7-nitro-1H-benzimidazol-1-yl)acetamide,
N-(1-{5-chloro-6-[2-fluoro-1-(fluoromethyl)ethoxy]pyridin-3-yl}ethyl)-2-(7-nitro-1H-benzimidazol-1-yl)acetamide,
N-(1-{6-[2-fluoro-1-(fluoromethyl)ethoxy]pyridin-3-yl}ethyl)-2-(7-nitro-1H-benzimidazol-1-yl)acetamide,
N-[(1S)-1-(4-{[(1S)-1-methylpropyl]oxy}phenyl)ethyl]-2-(7-nitro-1H-benzimidazol-1-yl)acetamide,
N-[(1S)-1-(4-ethoxyphenyl)ethyl]-2-(7-nitro-1H-benzimidazol-1-yl)acetamide,
N-[(1S)-1-(4-isopropoxyphenyl)ethyl]-2-(7-nitro-1H-benzimidazol-1-yl)acetamide,
N-[(3R)-5-Methoxy-3,4-dihydro-2H-chromen-3-yl]-2-(7-nitro-1H-benzimidazol-1-yl)acetamide,
N-[(3R)-8-Fluoro-5-methoxy-3,4-dihydro-2H-chromen-3-yl]-2-(7-nitro-1H-benzimidazol-1-yl)acetamide,
N-[1-(4-{[(2S)-2-methoxypropyl]oxy}phenyl)ethyl]-2-(7-nitro-1H-benzimidazol-1-yl)acetamide,
N-[1-(4-cyclopropylphenyl)ethyl]-2-(7-nitro-1H-benzimidazol-1-yl)acetamide,
N-[1-(4-ethynylphenyl)ethyl]-2-(7-nitro-1H-benzimidazol-1-yl)acetamide,
N-[1-(4-tert-butylphenyl)ethyl]-2-(6,7-difluoro-1H-benzimidazol-1-yl)acetamide,
N-[(1S)-1-(4-tert-butylphenyl)ethyl]-2-(6,7-difluoro-1H-benzimidazol-1-yl)acetamide,N-[1-(4-tert-butylphenyl)ethyl]-2-(7-cyano-1H-benzimidazol-1-yl)acetamide,
N-[1-(5-isopropoxypyridin-2-yl)ethyl]-2-(7-nitro-1H-benzimidazol-1-yl)acetamide,
N-[1-(5-tert-butyl-2-thienyl)ethyl]-2-(6,7-difluoro-1H-benzimidazol-1-yl)acetamide,
N-[1-(5-tert-butyl-2-thienyl)ethyl]-2-(7-cyano-1H-benzimidazol-1-yl)acetamide,
N-[1-(5-tert-butyl-2-thienyl)ethyl]-2-(7-fluoro-1H-benzimidazol-1-yl)acetamide,
N-[1-(5-tert-butylpyridin-2-yl)ethyl]-2-(7-fluoro-1H-benzimidazol-1-yl)acetamide,
N-[1-(6-isopropoxypyridin-3-yl)ethyl]-2-(7-nitro-1H-benzimidazol-1-yl)acetamide,
N-[2-(4-chlorophenyl)-1-methylethyl]-2-(7-nitro-1H-benzimidazol-1-yl)acetamide,
N-{(1S)-1-[4-(2-fluoroethoxy)phenyl]ethyl}-2-(7-nitro-1H-benzimidazol-1-yl)acetamide,
N-{(1S)-1-[4-(2-methoxy-1-methylethoxy)phenyl]ethyl}-2-(7-nitro-1H-benzimidazol-1-yl)acetamide,
N-{1-[3-chloro-5-(trifluoromethyl)pyridin-2-yl]ethyl}-2-(7-nitro-1H-benzimidazol-1-yl)acetamide,
N-{1-[4-(2,2-difluoroethoxy)phenyl]ethyl}-2-(7-nitro-1H-benzimidazol-1-yl)acetamide,
N-{1-[4-(cyclopentyloxy)-3-fluorophenyl]ethyl}-2-(7-nitro-1H-benzimidazol-1-yl)acetamide, N-{1-[4-[(1-Methylpiperidin-4-yl)oxy]-3-(trifluoromethyl)phenyl]ethyl}-2-(7-nitro-1H-benzimidazol-1-yl)acetamide,
N-{1-[4-{[(2S)-2-Methoxypropyl]oxy}-3-(trifluoromethyl)phenyl]ethyl}-2-(7-nitro-1H-benzimidazol-1-yl)acetamide,
N-{1-[5-(cyclopropylmethoxy)pyridin-2-yl]ethyl}-2-(7-nitro-1H-benzimidazol-1-yl)acetamide,
N-{1-[5-chloro-6-(2-fluoroethoxy)pyridin-3-yl]ethyl}-2-(7-nitro-1H-benzimidazol-1-yl)acetamide,
N-{1-[6-(2,2-difluoroethoxy)pyridin-3-yl]ethyl}-2-(7-nitro-1H-benzimidazol-1-yl)acetamide,
N-{1-[6-(2-fluoroethoxy)pyridin-3-yl]ethyl}-2-(7-nitro-1H-benzimidazol-1-yl)acetamide,
N-{1-[6-(cyclopentyloxy)pyridine-3-yl]ethyl}-2-(7-nitro-1H-benzimidazol-1-yl)acetamide, and
N-{1-methyl-2-[3-(trifluoromethyl)phenoxy]ethyl}-2-(7-nitro-1H-benzimidazol-1-yl)acetamide.

Another embodiment of the invention relates to compounds selected from the group consisting of
N-((1S)-1-{4-[2-fluoro-1-(fluoromethyl)ethoxy]phenyl}ethyl)-2-(7-nitro-1H-benzimidazol-1-yl)acetamide,
2-(7-nitro-1H-benzimidazol-1-yl)-N-{1-[6-(2,2,3,3-tetrafluoropropoxy)pyridin-3-yl]ethyl}acetamide,
N-[1-(4-tert-butylphenyl)ethyl]-2-(6,7-difluoro-1H-benzimidazol-1-yl)acetamide, and
N-[(1S)-1-(4-tert-butylphenyl)ethyl]-2-(6,7-difluoro-1H-benzimidazol-1-yl)acetamide Yet another embodiment of the invention relates to compounds selected from the group consisting of
2-(6,7-difluoro-1H-benzimidazol-1-yl)-N-{1-[4-(trifluoromethyl)phenyl]ethyl}acetamide,
2-(7-acetyl-1H-benzimidazol-1-yl)-N-(1-{4-[2-fluoro-1-(fluoromethyl)ethoxy]phenyl}ethyl)acetamide,
2-(7-chloro-1H-benzimidazol-1-yl)-N-(1-{4-[2-fluoro-1-(fluoromethyl)ethoxy]phenyl}ethyl)acetamide,
2-(7-chloro-1H-benzimidazol-1-yl)-N-(1-{4-[chloro(difluoro)methyl]phenyl}ethyl)acetamide,
2-(7-chloro-1H-benzimidazol-1-yl)-N-[1-(4-ethynylphenyl)ethyl]acetamide,
2-(7-chloro-1H-benzimidazol-1-yl)-N-{1-[4-(1,1,2,2-tetrafluoroethoxy)phenyl]ethyl}acetamide,
2-(7-chloro-1H-benzimidazol-1-yl)-N-{1-[4-(2,2-difluoroethoxy)phenyl]ethyl}acetamide,
2-(7-chloro-1H-benzimidazol-1-yl)-N-{1-[4-(trifluoromethyl)phenyl]ethyl}acetamide,
2-(7-cyano-1H-benzimidazol-1-yl)-N-(1-{4-[2-fluoro-1-(fluoromethyl)ethoxy]phenyl}ethyl)acetamide,
2-(7-cyano-1H-benzimidazol-1-yl)-N-[1-(4-isopropylphenyl)ethyl]acetamide,
2-(7-cyano-1H-benzimidazol-1-yl)-N-{1-[3-fluoro-4-(trifluoromethyl)phenyl]ethyl}acetamide,
2-(7-cyano-1H-benzimidazol-1-yl)-N-{1-[4-(2,2,2-trifluoroethoxy)phenyl]ethyl}acetamide,
2-(7-cyano-1H-benzimidazol-1-yl)-N-{1-[4-(trifluoromethoxy)phenyl]ethyl}acetamide,
2-(7-cyano-1H-benzimidazol-1-yl)-N-{1-[4-(trifluoromethyl)phenyl]ethyl}acetamide,
2-(7-cyano-1H-benzimidazol-1-yl)-N-{(1S)-1-[4-(trifluoromethyl)phenyl]ethyl}acetamide,
2-(7-cyano-1H-benzimidazol-1-yl)-N-{1-[4-[2-fluoro-1-(fluoromethyl)ethoxy]-2-(trifluoromethyl)phenyl]ethyl}acetamide,
2-(7-fluoro-1H-benzimidazol-1-yl)-N-[1-(4-isopropylphenyl)ethyl]acetamide, 2-(7-fluoro-1H-benzimidazol-1-yl)-N-{1-[4-(trifluoromethyl)phenyl]ethyl}acetamide,
2-(7-nitro-1H-benzimidazol-1-yl)-N-{1-[4-(1,1,2,2-tetrafluoroethoxy)phenyl]ethyl}acetamide,
2-(7-nitro-1H-benzimidazol-1-yl)-N-{1-[4-(2,2,2-trifluoroethoxy)phenyl]ethyl}acetamide,
2-(7-nitro-1H-benzimidazol-1-yl)-N-{1-[4-(trifluoromethoxy)phenyl]ethyl}acetamide,
2-(7-nitro-1H-benzimidazol-1-yl)-N-{1-[4-(trifluoromethyl)phenyl]ethyl}acetamide,
methyl(4-tert-butylphenyl){[(6,7-difluoro-1H-benzimidazol-1-yl)acetyl]amino}acetate,
N-((1S)-1-{4-[(1-methylprop-2-yn-1-yl)oxy]phenyl}ethyl)-2-(7-nitro-1H-benzimidazol-1-yl)acetamide,
N-((1S)-1-{4-[2-fluoro-1-(fluoromethyl)ethoxy]phenyl}ethyl)-2-(7-nitro-1H-benzimidazol-1-yl)acetamide,
N-(1-{2-chloro-4-[2-fluoro-1-(fluoromethyl)ethoxy]phenyl}ethyl)-2-(7-cyano-1H-benzimidazol-1-yl)acetamide,
N-(1-{4-[chloro(difluoro)methyl]phenyl}ethyl)-2-(7-nitro-1H-benzimidazol-1-yl)acetamide,
N-[(1S)-1-(4-{[(1S)-1-methylpropyl]oxy}phenyl)ethyl]-2-(7-nitro-1H-benzimidazol-1-yl)acetamide,
N-[(1S)-1-(4-ethoxyphenyl)ethyl]-2-(7-nitro-1H-benzimidazol-1-yl)acetamide,
N-[(1S)-1-(4-isopropoxyphenyl)ethyl]-2-(7-nitro-1H-benzimidazol-1-yl)acetamide,
N-[1-(4-{[(2S)-2-methoxypropyl]oxy}phenyl)ethyl]-2-(7-nitro-1H-benzimidazol-1-yl)acetamide,
N-[1-(4-cyclopropylphenyl)ethyl]-2-(7-nitro-1H-benzimidazol-1-yl)acetamide,
N-[1-(4-ethynylphenyl)ethyl]-2-(7-nitro-1H-benzimidazol-1-yl)acetamide,
N-[1-(4-tert-butylphenyl)ethyl]-2-(6,7-difluoro-1H-benzimidazol-1-yl)acetamide,
N-[(1S)-1-(4-tert-butylphenyl)ethyl]-2-(6,7-difluoro-1H-benzimidazol-1-yl)acetamide,
N-[1-(4-tert-butylphenyl)ethyl]-2-(7-cyano-1H-benzimidazol-1-yl)acetamide,
N-{(1S)-1-[4-(2-fluoroethoxy)phenyl]ethyl}-2-(7-nitro-1H-benzimidazol-1-yl)acetamide,
N-{(1S)-1-[4-(2-methoxy-1-methylethoxy)phenyl]ethyl}-2-(7-nitro-1H-benzimidazol-1-yl)acetamide,
N-{1-[4-(2,2-difluoroethoxy)phenyl]ethyl}-2-(7-nitro-1H-benzimidazol-1-yl)acetamide,
N-{1-[4-(cyclopentyloxy)-3-fluorophenyl]ethyl}-2-(7-nitro-1H-benzimidazol-1-yl)acetamide,
N-{1-[4-[(1-Methylpiperidin-4-yl)oxy]-3-(trifluoromethyl)phenyl]ethyl}-2-(7-nitro-1H-benzimidazol-1-yl)acetamide, and
N-{1-[4-{[(2S)-2-Methoxypropyl]oxy}-3-(trifluoromethyl)phenyl]ethyl}-2-(7-nitro-1H-benzimidazol-1-yl)acetamide.

One embodiment of the invention relates to compounds selected from the group consisting of
N-{1-[6-(2-fluoroethoxy)pyridin-3-yl]ethyl}-2-(7-nitro-1H-benzimidazol-1-yl)acetamide,
N-(1-{6-[2-fluoro-1-(fluoromethyl)ethoxy]pyridin-3-yl}ethyl)-2-(7-nitro-1H-benzimidazol-1-yl)acetamide,
N-{1-[6-(cyclopentyloxy)pyridine-3-yl]ethyl}-2-(7-nitro-1H-benzimidazol-1-yl)acetamide,
N-(1-{5-chloro-6-[2-fluoro-1-(fluoromethyl)ethoxy]pyridin-3-yl}ethyl)-2-(7-nitro-1H-benzimidazol-1-yl)acetamide,
2-(7-nitro-1H-benzimidazol-1-yl)-N-{1-[5-(trifluoromethyl)pyridin-2-yl]propyl}acetamide,
2-(7-nitro-1H-benzimidazol-1-yl)-N-{1-[5-(trifluoromethyl)pyridin-2-yl]ethyl}acetamide,
2-(7-chloro-1H-benzimidazol-1-yl)-N-{1-[3-chloro-5-(trifluoromethyl)pyridin-2-yl]ethyl}acetamide,
N-{1-[3-chloro-5-(trifluoromethyl)pyridin-2-yl]ethyl}-2-(7-nitro-1H-benzimidazol-1-yl)acetamide,
N-{1-[5-chloro-6-(2-fluoroethoxy)pyridin-3-yl]ethyl}-2-(7-nitro-1H-benzimidazol-1-yl)acetamide,
2-(7-Chloro-benzoimidazol-1-yl)-N-[1-(6-isopropoxy-pyridin-3-yl)-ethyl]-acetamide,
N-[1-(6-isopropoxypyridin-3-yl)ethyl]-2-(7-nitro-1H-benzimidazol-1-yl)acetamide,
N-{1-[5-(cyclopropylmethoxy)pyridin-2-yl]ethyl}-2-(7-nitro-1H-benzimidazol-1-yl)acetamide,
N-[1-(5-isopropoxypyridin-2-yl)ethyl]-2-(7-nitro-1H-benzimidazol-1-yl)acetamide,
N-[1-(5-tert-butylpyridin-2-yl)ethyl]-2-(7-fluoro-1H-benzimidazol-1-yl)acetamide,
N-[1-(5-tert-butyl-2-thienyl)ethyl]-2-(7-fluoro-1H-benzimidazol-1-yl)acetamide,
N-[1-(5-tert-butyl-2-thienyl)ethyl]-2-(7-cyano-1H-benzimidazol-1-yl)acetamide,
2-(7-nitro-1H-benzimidazol-1-yl)-N-{1-[6-(2,2,2-trifluoroethoxy)pyridin-3-yl]ethyl}acetamide,
2-(7-chloro-1H-benzimidazol-1-yl)-N-{1-[6-(2,2,2-trifluoroethoxy)pyridin-3-yl]ethyl}acetamide,
2-(7-nitro-1H-benzimidazol-1-yl)-N-{1-[6-(2,2,3,3-tetrafluoropropoxy)pyridin-3-yl]ethyl}acetamide,
2-(7-chloro-1H-benzimidazol-1-yl)-N-{1-[6-(2,2,3,3-tetrafluoropropoxy)pyridin-3-yl]ethyl}acetamide,
N-{1-[6-(2,2-difluoroethoxy)pyridin-3-yl]ethyl}-2-(7-nitro-1H-benzimidazol-1-yl)acetamide, and
N-[1-(5-tert-butyl-2-thienyl)ethyl]-2-(6,7-difluoro-1H-benzimidazol-1-yl)acetamide.

A yet further embodiment of the invention relates to compounds selected from the group consisting of
N-[1-(6-tert-butyl-2-methoxypyridin-3-yl)ethyl]-2-(7-cyano-1H-benzimidazol-1-yl)acetamide,
N-[1-(6-tert-butyl-2-methylpyridin-3-yl)ethyl]-2-(6,7-difluoro-1H-benzimidazol-1-yl)acetamide,
N-[1-(6-tert-butyl-4-methylpyridin-3-yl)ethyl]-2-(7-cyano-1H-benzimidazol-1-yl)acetamide,
N-[1-(6-tert-butyl-2-chloropyridin-3-yl)ethyl]-2-(7-cyano-1H-benzimidazol-1-yl)acetamide,
N-[1-(6-tert-butylpyridin-3-yl)ethyl]-2-(7-cyano-1H-benzimidazol-1-yl)acetamide,
N-[1-(4-tert-butylphenyl)ethyl]-2-(7-cyano-1H-benzimidazol-1-yl)acetamide, and
2-(7-acetyl-1H-benzimidazol-1-yl)-N-[(1S)-1-(4-tert-butylphenyl)ethyl]acetamide Listed below are definitions of various terms used in the specification and claims to describe the present invention.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification '$C_{1-3}$' means a carbon group having 1, 2 or 3 carbon atoms, '$C_{1-6}$' means a carbon group having 1, 2, 3, 4, 5 or 6 carbon atoms, and '$C_{3-7}$' means a carbon group having 3, 4, 5, 6 or 7 carbon atoms, In this specification, unless stated otherwise, the term "alkyl" includes both straight and branched chain alkyl groups and may be, but are not limited to methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl.

The term "amine" or "amino" refers to radicals of the general formula —NRR', wherein R and R' are independently selected from hydrogen or a hydrocarbyl radical.

The term "aromatic" refers to hydrocarbyl radicals having one or more polyunsaturated carbon rings having aromatic character, (e.g., 4n+2 delocalized electrons) and comprising 6 up to about 14 carbon atoms.

The term "aryl" used alone or as suffix or prefix, refers to a hydrocarbon radical having one or more polyunsaturated carbon rings having aromatic character, (e.g., 4n+2 delocalized electrons) and comprising 5 up to about 14 carbon atoms, wherein the radical is located on a carbon of the aromatic ring.

In this specification, unless stated otherwise, the term "cycloalkyl" refers to an optionally substituted, saturated cyclic hydrocarbon ring system. The term "$C_{3-7}$cycloalkyl" may be cyclopropyl, cyclobutyl, cyclopentyl, cyclohexyl or cycloheptyl.

The term "heterocycle" or "heterocyclic" or "heterocyclic moiety" refers to ring-containing monovalent and divalent radicals having one or more heteroatoms, independently selected from N, O, P and S, as part of the ring structure and comprising at least 3 and up to about 20 atoms in the rings preferably 5 and 6 membered rings. Heterocyclic moieties may be saturated or unsaturated, containing one or more double bonds, and heterocyclic moieties may contain more than one ring.

The term "heterocycloalkyloxy" denotes a 3- to 7-membered, non-aromatic, partially or completely saturated hydrocarbon group, which contains one ring and at least one heteroatom. Examples of said heterocycle include, but are not limited to pyrrolidinyloxy, pyrrolidonyloxy, piperidinyloxy, piperazinyloxy, morpholinyloxy, oxazolyloxy, 2-oxazolidonyloxy or tetrahydrofuranyloxy.

In this specification, unless stated otherwise, the term "heteroaryl" refers to an optionally substituted monocyclic or bicyclic unsaturated aromatic ring system containing at least one heteroatom selected independently form N, O or S. Examples of "heteroaryl" may be, but are not limited to pyridyl, pyrrolyl, furyl, thienyl, imidazolyl, oxazolyl, isoxazolyl, thiazolyl, pyrazolyl, benzofuryl, indolyl, isoindolyl, benzimidazolyl, pyridazinyl, pyrimidinyl, pyrazinyl, tetrazolyl, triazolyl or oxazolyl.

In this specification, unless stated otherwise, the terms "arylalkyl" and "heteroarylalkyl" refer to a substituent that is attached via the alkyl group to an aryl or heteroaryl group.

In this specification, unless stated otherwise, the terms "halo" and "halogen" may be fluoro, iodo, chloro or bromo.

In this specification, unless stated otherwise, the term "haloalkyl" means an alkyl group as defined above, which is substituted with halo as defined above. The term "$C_{1-6}$haloalkyl" may include, but is not limited to fluoromethyl, difluoromethyl, trifluoromethyl, fluoroethyl, difluoroethyl or bromopropyl.

The present invention relates to the compounds of the invention as hereinbefore defined as well as to the salts, solvates or solvated salts thereof. Salts for use in pharmaceutical compositions will be pharmaceutically acceptable salts, but other salts may be useful in the production of the compounds of the invention.

A suitable pharmaceutically acceptable salt of the compounds of the invention is, for example, an acid-addition salt, for example an inorganic or organic acid. In addition, a suitable pharmaceutically acceptable salt of the compounds of the invention is an alkali metal salt, an alkaline earth metal salt or a salt with an organic base.

Other pharmaceutically acceptable salts and methods of preparing these salts may be found in, for example, Remington's Pharmaceutical Sciences (18th Edition, Mack Publishing Co.).

Some compounds of the invention may have chiral centres and/or geometric isomeric centres (E- and Z-isomers), and it is to be understood that the invention encompasses all such optical, diastereoisomeric and geometric isomers.

The invention also relates to any and all tautomeric forms of the compounds of the invention.

Methods of Preparation

Some compounds of the present invention may be prepared according to the methods described in PCT/SE2004/000738.

Another aspect of the present invention provides processes for preparing compounds of formula I, or salts, solvates or solvated salts thereof.

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). For representative examples of heterocyclic chemistry see for example "Heterocyclic Chemistry", J. A. Joule, K. Mills, G. F. Smith, 3rd ed. Chapman and Hall (1995), p. 189-224 and "Hetero-cyclic Chemistry", T. L. Gilchrist, 2nd ed. Longman Scientific and Technical (1992), p. 248-282.

The term "room temperature" and "ambient temperature" shall mean, unless otherwise specified, a temperature between 16 and 25° C.

Methods of Preparation

One embodiment of the invention relates to processes for the preparation of the compound of formula I according to the General Method A or Method B, wherein $R^1$ through $R^4$, are defined as in formula I, comprising;

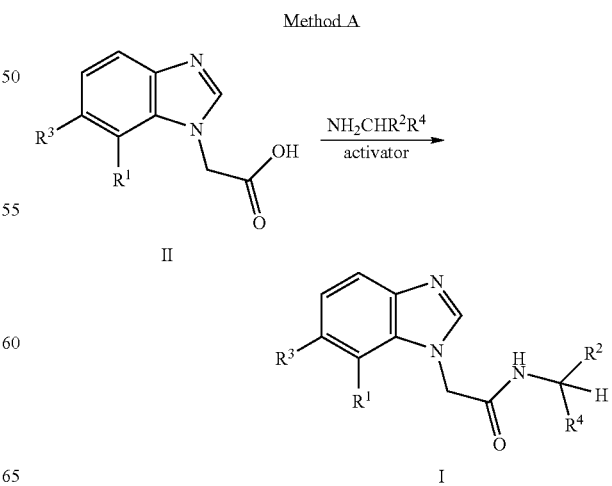

whereby the target compound of formula I is obtained from the benzimidazolylacetic acid of formula II or its deprotonated form, via its conversion into an activated form, i.e. either the acyl chloride by treatment with oxalyl chloride or the mixed anhydride by treatment with O-(7-azabenzotriazol1-yl)-N,N,N',N'-tetramethyluronium hexafluorophosphate and further treatment with an appropriate amine $NH_2CHR^2R^4$. This reaction may be performed in any manner known to the skilled man in the art. The activation may be performed using any other similar activating reagent like 1,3-dicyclohexylcarbodiimide, 1-ethyl-3-(3-dimethylaminopropyl)carbodiimide hydrochloride or 1,1'-carbonyldiimidazole. Suitable solvents to be used for this reaction may be halogenated hydrocarbons such as chloroform, dichloromethane and dichloroethane or aromatic and heteroaromatic compounds such as benzene, toluene, xylene, pyridine and lutidine or ethers such as ethyl ether, tetrahydrofuran and dioxan or aprotic polar solvents like acetonitrile and dimethylformamide, or any mixtures thereof. Catalysts such as heteroaromatic bases like pyridine and lutidine or tertiary amines like triethylamine, N-methylmorpholine and ethyl diisopropylamine may be used as well. The temperature may be between −30 and 50° C. and the reaction time between 1 and 30 h.

Starting materials, the acids of formula II, may be obtained using multistep procedures described in detail in the following examples of synthesis, starting from commercially available appropriately 1,2,3-trisubstituted benzenes and 1,2,3,4-tetrasubstituted benzenes.

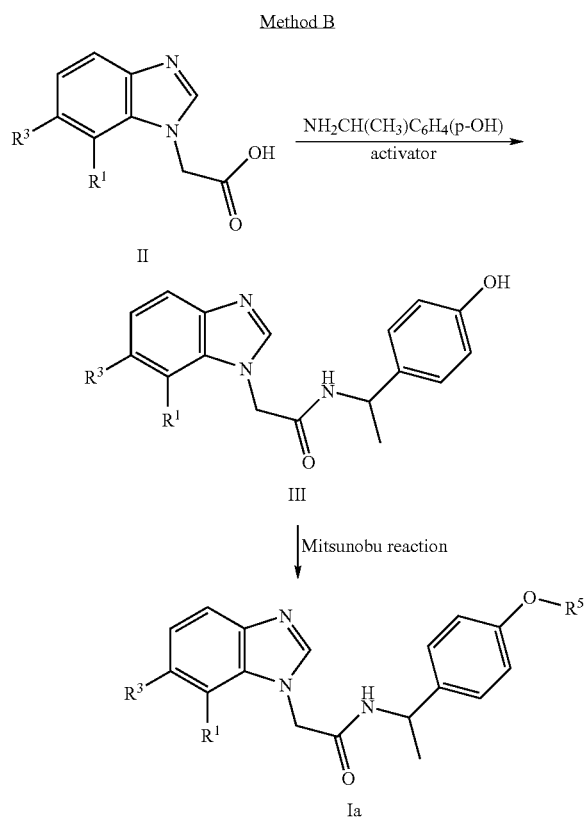

Method B whereby the target compound of formula Ia is obtained by two-step procedure from the benzimidazolylacetic acid of formula II or its deprotonated form. The first step includes conversion of acid II into intermediate III according to the procedure of Method A, while at the second step the intermediate is converted into the final product in Mitsunobu conditions using an appropriate alcohol $R^5OH$.

Intermediates

A further embodiment of the invention relates to compounds selected from the group consisting of
N-[(1S)-1-(4-hydroxyphenyl)ethyl]-2-(7-nitro-1H-benzimidazol-1-yl)acetamide,
1-[6-(2-fluoroethoxy)pyridin-3-yl]ethanamine,
1-[6-(2,2,2-trifluoroethoxy)pyridin-3-yl]ethanamine,
1-[6-(2,2-difluoroethoxy)pyridin-3-yl]ethanamine,
1-[6-(2,2,3,3-tetrafluoropropoxy)pyridin-3-yl]ethanamine,
1-[6-(cyclopentyloxy)pyridin-3-yl]ethanamine,
1-(4-{[(2S)-2-methoxypropyl]oxy}phenyl)ethanamine,
1-[4-(2,2,2-trifluoroethoxy)phenyl]ethanamine,
1-[4-[(1-Methylpiperidin-4-yl)oxy]-3-(trifluoromethyl)phenyl]ethanamine,
1-[4-{[(2S)-2-Methoxypropyl]oxy}-3-(trifluoromethyl)phenyl]ethanamine,
(6,7-difluoro-1H-benzimidazol-1-yl)acetic acid,
[(5-tert-butyl-2-thienyl)methyl]amine,
[1-(5-tert-butylpyridin-2-yl)ethyl]amine,
6-tert-butyl-4-methylnicotinonitrile,
[1-(6-tert-butylpyridin-3-yl)ethyl]amine,
[1-(6-tert-butyl-2-chloropyridin-3-yl)ethyl]amine,
[1-(6-tert-butyl-2-methoxypyridin-3-yl)ethyl]amine,
[1-(6-tert-butyl-4-methylpyridin-3-yl)ethyl]amine,
6-tert-butyl-2-methylnicotinonitrile, and
[1-(6-tert-butyl-2-methylpyridin-3-yl)ethyl]amine.

Another embodiment relates to the use of these compounds as intermediates in the preparation of compounds of the invention.

Pharmaceutical Composition

According to one embodiment of the present invention there is provided a pharmaceutical composition comprising as active ingredient a therapeutically effective amount of the compound of the invention, or salts, solvates or solvated salts thereof, in association with one or more pharmaceutically acceptable diluents, excipients and/or inert carriers.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration e.g. as an ointment, patch or cream or for rectal administration e.g. as a suppository.

In general the above compositions may be prepared in a conventional manner using one or more conventional excipients, pharmaceutical acceptable diluents and/or inert carriers. Suitable daily doses of the compounds of the invention in the treatment of a mammal, including man, are approximately 0.01 to 250 mg/kg bodyweight at peroral administration and about 0.001 to 250 mg/kg bodyweight at parenteral administration.

The typical daily dose of the active ingredient varies within a wide range and will depend on various factors such as the relevant indication, severity of the illness being treated, the route of administration, the age, weight and sex of the patient and the particular compound being used, and may be determined by a physician.

Examples of Pharmaceutical Composition

The following illustrate representative pharmaceutical dosage forms containing a compound of the invention, or salts, solvates or solvated salts thereof, (hereafter compound X), for preventive or therapeutic use in mammals:

| (a): Tablet | mg/tablet |
|---|---|
| Compound X | 100 |
| Lactose | 182.75 |
| Croscarmellose sodium | 12.0 |
| Maize starch paste (5% w/v paste) | 2.25 |
| Magnesium stearate | 3.0 |
| (b): Capsule | mg/capsule |
| Compound X | 10 |
| Lactose | 488.5 |
| Magnesium stearate | 1.5 |
| (c): Injection | (50 mg/ml) |
| Compound X | 5.0% w/v |
| 1M Sodium hydroxide solution | 15.0% v/v |
| 0.1M Hydrochloric acid | (to adjust pH to 7.6) |
| Polyethylene glycol 400 | 45% w/v |
| Water for injection | up to 100% |

The above compositions may be obtained by conventional procedures well known in the pharmaceutical art.

Medical Use

Surprisingly, it has been found that the compounds according to the present invention are useful in therapy. The compounds of the invention, or salts, solvates or solvated salts thereof, as well as their corresponding active metabolites, exhibit a high degree of potency and selectivity for individual vanilloid receptor 1 (VR1) groups. Accordingly, the compounds of the present invention are expected to be useful in the treatment of conditions associated with excitatory activation of vanilloid receptor 1 (VR1).

The compounds may be used to produce an inhibitory effect of VR1 in mammals, including man.

VR1 are highly expressed in the peripheral nervous system and in other tissues. Thus, it is expected that the compounds of the invention are well suited for the treatment of VR1 mediated disorders.

The compounds of the invention are expected to be suitable for the treatment of acute and chronic pain, acute and chronic neuropathic pain and acute and chronic inflammatory pain.

Examples of such disorder may be selected from the group comprising low back pain, post-operative pain, visceral pains like chronic pelvic pain and the like.

The compounds of the invention are also expected to be suitable for the treatment of acute and chronic nociceptive pain.

Further relevant disorders may be selected from the group comprising cystitis, including interstitial cystitis and pain related thereto, ischeamic, sciatia, diabetic neuropathy, multiple sclerosis, arthritis, osteoarthritis, rheumatoid arthritis, fibromyalgia, pain and other signs and symptoms associated with psoriasis, pain and other signs and symptoms associated with cancer, emesis, urinary incontinence, hyperactive bladder and HIV neuropathy.

Additional relevant disorders may be selected from the group comprising gastro-esophageal reflux disease (GERD), irritable bowel syndrome (IBS), inflammatory bowel disease (IBD) and pancreatitis.

Other relevant disorders are related to respiratory diseases and may be selected from the group comprising asthma, cough, chronic obstructive lung disease, specifically chronic obstructive pulmonary disease (COPD) and emphysema, lung fibrosis and interstitial lung disease.

Yet other relevant disorders are obesity and obesity-related diseases or disorders, or migraine.

In one embodiment the obesity or obesity-related diseases or disorders is selected from the following: type 1 diabetes, type 2 diabetes, impaired glucose tolerance, cardiovascular disease, hypertension, insulin resistance, cancer and reproductive disorders.

The VR1 inhibitor(s) may be administrated by either an oral or inhaled route. The respiratory disease may be an acute and chronic illness and may be related to infection(s) and/or exposure to environmental pollution and/or irritants.

The compounds of the invention may also be used as antitoxin to treat (over-) exposure to VR1 activators like capsaicin, tear gas, acids or heat. Regarding heat, there is a potential use for VR1 antagonists in (sun-) burn induced pain, or inflammatory pain resulting from burn injuries.

The compounds may further be used for treatment of tolerance to VR1 activators.

One embodiment of the invention relates to the compounds of the invention as hereinbefore defined, for use as a medicament.

Another embodiment of the invention relates to the compounds of the invention as hereinbefore defined, for use as a medicament for treatment of VR1 mediated disorders.

A further embodiment of the invention relates to the compounds of the invention as hereinbefore defined, for use as a medicament for treatment of acute and chronic pain disorders.

Another embodiment of the invention relates to the compounds of the invention as hereinbefore defined for use as a medicament for treatment of acute and chronic nociceptive pain.

Yet another embodiment of the invention relates to the compounds of the invention as hereinbefore defined, for use as a medicament for treatment of acute and chronic neuropathic pain.

Yet a further embodiment of the invention relates to the compounds of the invention as hereinbefore defined, for use as a medicament for treatment of acute and chronic inflammatory pain.

One embodiment of the invention relates to the compounds of the invention as hereinbefore defined, for use as a medicament for treatment of low back pain, post-operative pain and visceral pains like chronic pelvic pain.

Another embodiment of the invention relates to the compounds of the invention as hereinbefore defined, for use as a medicament for treatment of cystitis, including interstitial cystitis and pain related thereto, ischeamic, sciatia, diabetic neuropathy, multiple sclerosis, arthritis, osteoarthritis, rheumatoid arthritis, fibromyalgia, pain and other signs and symptoms associated with psoriasis, pain and other signs and symptoms associated with cancer, emesis, urinary incontinence, hyperactive bladder and HIV neuropathy.

A further embodiment of the invention relates to the compounds of the invention as hereinbefore defined, for use as a medicament for treatment of gastro-esophageal reflux disease (GERD), irritable bowel syndrome (IBS), inflammatory bowel disease (IBD) and pancreatitis.

Yet a further embodiment of the invention relates to the compounds of the invention as hereinbefore defined, for use as a medicament for treatment of respiratory diseases selected from the group comprising asthma, cough, chronic obstructive pulmonary disease (COPD), chronic obstructive lung disease and emphysema, lung fibrosis and interstitial lung disease.

One embodiment of the invention relates to the use of the compound of the invention as hereinbefore defined, in the manufacture of a medicament for treatment of VR1 mediated disorders and for treatment of acute and chronic pain disorders, acute and chronic neuropathic pain and acute and chronic inflammatory pain, and respiratory diseases and any other disorder mentioned above.

Another embodiment of the invention relates to a method of treatment of VR1 mediated disorders and acute and chronic pain disorders, acute and chronic neuropathic pain and acute and chronic inflammatory pain, and respiratory diseases, and any other disorder mentioned above, comprising administrering to a mammal, including man in need of such treatment, a therapeutically effective amount of the compounds of the invention, as hereinbefore defined.

A further embodiment of the invention relates to a pharmaceutical composition comprising a compound of the invention as hereinbefore defined, for use in treatment of VR1 mediated disorders and for treatment of acute and chronic pain disorders, acute and chronic neuropathic pain and acute and chronic inflammatory pain, and respiratory diseases, and any other disorder mentioned above.

In the context of the present specification, the term "therapy" and "treatment" includes prevention and prophylaxis, unless there are specific indications to the contrary. The terms "treat", "therapeutic" and "therapeutically" should be construed accordingly.

In this specification, unless stated otherwise, the term "inhibitor" and "antagonist" mean a compound that by any means, partly or completely, blocks the transduction pathway leading to the production of a response by the ligand.

The term "disorder", unless stated otherwise, means any condition and disease associated with vanilloid receptor activity.

Non-Medical Use

In addition to their use in therapeutic medicine, the compounds of the invention, or salts, solvates or solvated salts thereof, are also useful as pharmacological tools in the development and standardisation of in vitro and in vivo test systems for the evaluation of the effects of inhibitors of VR1 related activity in laboratory animals such as cats, dogs, rabbits, monkeys, rats and mice, as part of the search for new therapeutics agents.

EXAMPLES

The invention will now be illustrated by the following non-limiting examples.

Abbreviations
DCE dichloroethane
DCM dichloromethane
DMAP dimethylaminopyridine
EDC 1-(3-dimethylaminopropyl)-3-ethylcarbodiimide hydrochloride
HATU O-(7-azabenzotriazol-1-yl)-N,N,N',N'-tetramethyluronium hexafluorophosphate
HPLC high performance liquid chromatography
LC liquid chromatography
MS mass spectometry
ret. time retention time
TFA trifluoroacetic acid
THF tetrahydrofuran
DMF dimethylformamide
TMEDA tetramethylethylenediamine
EtOAc ethyl acetate General Methods All starting materials are commercially available or described in the literature. The $^1$H NMR spectra were recorded on Brucker at 400 MHz. The mass spectra were recorded utilising electrospray (LC-MS; LC:Waters 2790, column XTerra MS $C_8$ 2.5 µm 2.1×30 mm, buffer gradient $H_2O$+0.1% TFA:$CH_3CN$+0.04% TFA, MS: micromass ZMD//ammonium acetate buffer) ionisation techniques.

Synthesis of the Intermediates: 7-substituted 1H-benzimidazol-1-yl-acetic acids, 1)-5)

1) (7-Nitro-1H-benzimidazol-1-yl)acetic acid—this synthesis is described in WO2004/100865.
2) (7-chloro-1H-benzimidazol-1-yl)acetic acid—this synthesis is described in WO2004/100865.
3) (6,7-difluoro-1H-benzimidazol-1-yl)acetic acid

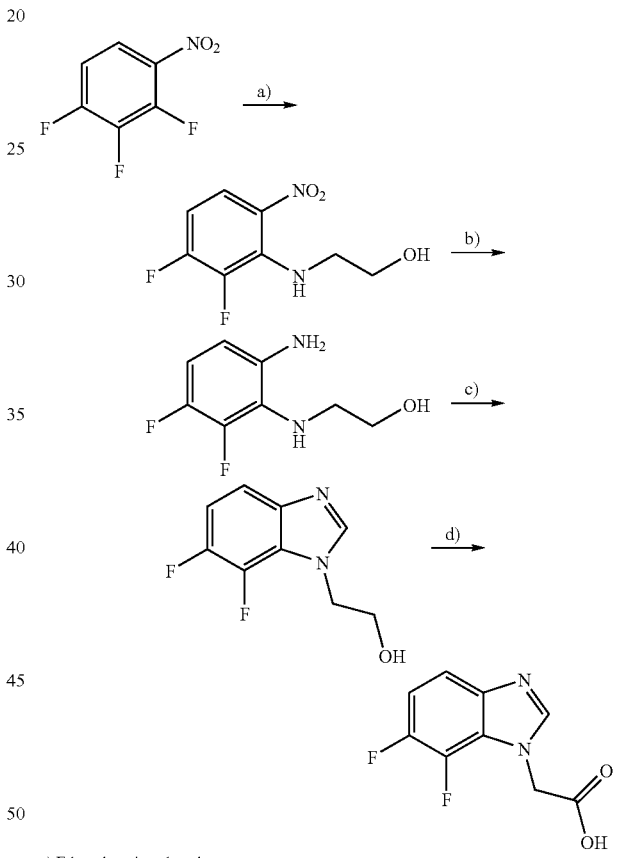

a) Ethanol, aminoethanol,
b) Pd/C 10%, ethanol, ethyl acetate
c) 1-formic acid, 2-2N $NH_3$ ethanol
d) TEMPO, $NaClO_2$, NaClO, MeCN, 6.8 Phosphate buffer A 2-[(2,3-difluoro-6-nitrophenyl)amino]ethanol:

A solution of 1,2,3-trifluoro-4-nitrobenzene (5.0 g, 28.2 mmol) and ethanolamine (1.72 g, 28.2 mmol) in 100 ml of ethanol is stirred over night at room temperature then at 70° C. for 5 hours. The reaction is concentrated to dryness and purified by silica gel flash chromatography using a gradient of 80/20 to 20/80 heptane/ethyl acetate providing an orange solid. Yield (3.8 g, 62%). $^1$H NMR (400 MHz, $CDCl_3$) δ ppm 1.67 (t, J=5.08 Hz, 1 H) 3.77-3.83 (m, 2 H) 3.88-3.94 (m, 2 H) 6.51 (ddd, J=9.77, 8.59, 7.03 Hz, 1 H) 8.02 (ddd, J=9.77, 5.66, 2.34 Hz, 1 H) 8.21 (s, 1 H)

B 2-[(6-amino-2,3-difluorophenyl)amino]ethanol:

To a solution of 2-[(2,3-difluoro-6-nitrophenyl)amino]ethanol (3.8 g, 17.4 mmol) in 70 ml of ethyl acetate and 30 ml of ethanol is added 10% Pd/C (380 mg). The reaction is shaken under 50 PSI of hydrogen for 3 hours. The pressure is periodically adjusted to 50 PSI. The reaction is filtered through celite, rinsed with ethanol and concentrated. The resulting material is used without further purification in the next step. $^1$H NMR (400 MHz, CDCl$_3$) δ ppm 3.17-3.27 (m, 2 H) 3.68-3.78 (m, 2 H) 6.38 (ddd, J=8.89, 4.69, 2.05 Hz, 1 H) 6.61-6.70 (m, 1 H)

C 2-(6,7-difluoro-1H-benzimidazol-1-yl)ethanol:

A solution of 2-[(6-amino-2,3-difluorophenyl)amino]ethanol in 100 ml of formic acid is heated at 100° C. for 2 hours. The reaction is concentrated to dryness, taken into 100 ml of 2 N NH$_3$ in ethanol and stirred for 2.5 hrs. The reaction is concentrated and taken into ethyl acetate. The resulting precipitate is collected by filtration and rinsed with cold ethyl acetate. The mother liquor is concentrated and purified by silica gel flash chromatography using ethyl acetate/heptane. The combined yield is 3.2 g or 93% for two steps based on 3.8 g of 2-[(2,3-difluoro-6-nitrophenyl)amino]ethanol. $^1$H NMR (400 MHz, CDCl$_3$) δ ppm 4.06 (dt, J=4.78, 0.98 Hz, 2 H), 4.39 (t, J=4.78 Hz, 2 H), 6.92 (ddd, J=11.03, 8.89, 7.42 Hz, 1 H), 7.12 (ddd, J=8.89, 3.71, 1.27 Hz, 1 H), 7.76 (s, 1 H)

D (6,7-difluoro-1H-benzimidazol-1-yl)acetic acid.

2-(6,7-difluoro-1H-benzimidazol-1-yl)ethanol (2.96 g, 15 mmol) is taken into 75 ml of MeCN and sodium phosphate buffer (56 ml, 0.67 M, pH 6.8) and the mixture is heated to 42° C. Tempo (165 mg, 1.05 mol) is added followed by the simultaneous dropwise addition of a solution of NaClO$_2$ (3.38 g, 80% pure, 30 mmol in 15 ml water) and a solution of bleach (350 μL of 6% NaOCl in 7.5 mL water) over 1.5 hours. After 48 hrs, the same quantities of NaClO$_2$ and bleach are added. After a further 24 hours, Tempo (165 mg, 1.05 mol) is added and the reaction is stirred for 72 hrs. The darkened reaction is allowed to cool to room temperature followed by the dropwise addition of 30 ml of a saturated solution of Na$_2$SO$_3$ (exothermic). The reaction becomes almost colourless. Using 2 N NaOH, the pH is raised to 9.2 and the reaction is extracted 4 times with ethyl acetate. The pH is then lowered to 3.8 with 2 N HCl and the solution allowed to stand for 48 hours. 1.98 grams of white crystalline material is recovered. The mother liquor is reduced to half the volume and allowed to stand. A further 260 mg is collected. (Combined yield 2.23 g, 70%)

$^1$H NMR (400 MHz, DMSO-D6) δ ppm 5.19 (s, 2 H) 7.25 (ddd, J=11.62, 8.89, 7.62 Hz, 1 H) 7.49 (ddd, J=8.94, 3.86, 1.07 Hz, 1 H) 8.13-8.28 (m, 1 H) 13.38 (s, 1 H)

4) (7-Cyano-1H-benzimidazol-1-yl)acetic acid—this synthesis is described in WO2004/100865, Example 12.

5) (7-Acetyl-1H-benzimidazol-1-yl)acetic acid

A. 1-[1-(2-Hydroxyethyl)-1H-benzimidazol-7-yl]ethanone.

A solution of 1-(2-hydroxyethyl)-1H-benzimidazole-7-carbonitrile (0.29 g, 1.5 mmol) in dry THF (6.2 ml) was cooled to –78° C. and MeLi (5.8 mL, 9.3 mmol) was added slowly. After the addition the reaction mixture was allowed to warm up to ambient temperature and kept such for 30 min. Then the temperature was brought down to –78° C. again and water (4 ml) was added slowly. After warming up the reaction mixture was acidified to pH 4 and heated at 50° C. for 30 min. Solvents were removed under reduced pressure and the residue was partitioned between ethyl acetate and aq. NaHCO$_3$. The organic extract was further washed with water and brine, dried over Na$_2$SO$_4$ and concentrated. Purification was performed on flash silica column using ethyl acetate—methanol as the eluent.

Yield 0.25 g (80%). Calculated for C$_{11}$H$_{12}$N$_2$O$_3$ m/z: 204.23, found 205.23 [M+H]$^+$.

$^1$H NMR (400 MHz, DMSO-D6) δ ppm 2.67 (s, 3 H) 3.51 (q, J=5.1 Hz, 2 H) 4.41 (t, J=5.3 Hz, 2 H) 4.77 (t, J=5.1 Hz, 1 H) 7.29 (t, J=7.8 Hz, 1 H) 7.78 (dd, J=7.6, 1.0 Hz, 1 H) 7.88 (dd, J=8.1, 1.0 Hz, 1 H) 8.20 (s, 1 H).

B. The title compound: (7-acetyl-1H-benzimidazol-1-yl)acetic acid, was prepared and isolated as a triethylammonium salt according to the procedure described for the synthesis of (7-Cyano-1H-benzimidazol-1-yl)acetic acid (part D). Yield 116 mg (30%). Calculated for C$_{11}$H$_{10}$N$_2$O$_3$ m/z: 218.21, found 219.16 [M+H]$^+$. $^1$H NMR (400 MHz, DMSO-D6) δ ppm 1.02 (t, J=7.1 Hz, 9 H) 2.56 (s, 3 H) 2.68-2.77 (m, 6 H) 4.91 (s, 2 H) 7.24 (t, J=7.8 Hz, 1 H) 7.70 (d, J=7.6 Hz, 1 H) 7.81-7.85 (m, 1 H) 8.16 (s, 1 H).

Syntheses of the Intermediates: amines, 6)-16)

6) N-[(1S)-1-(4-hydroxyphenyl)ethyl]-2-(7-nitro-1H-benzimidazol-1-yl)acetamide

The title compound was synthesised according to the general method of synthesis of target compounds (see below) from (7-nitro-1H-benzimidazol-1-yl)acetic acid and 4-[(1S)-1-aminoethyl]phenol. $^1$H NMR (400 MHz, DMSO-d$_6$) δ ppm 9.26 (s, 1 H) 8.55 (d, J=8.03 Hz, 1 H) 8.40 (s, 1 H) 8.10 (d, J=8.03 Hz, 1 H) 7.98 (d, J=7.53 Hz, 1 H) 7.39 (t, J=8.03 Hz, 1 H) 7.05-7.15 (m, 2 H) 6.64-6.75 (m, 2 H) 5.19 (s, 2 H) 4.71-4.83 (m, 1 H) 1.32 (d, J=6.78 Hz, 3 H). MS (ESI) m/z: 341 [M+H]

7) 1-[6-(2,2,2-trifluoroethoxy)pyridin-3-yl]ethanamine

A. 6-(2,2,2-trifluoroethoxy)nicotinonitrile

To 6-chloronicotinonitrile (0.30 g, 2.2 mmol) was a mixture of 2,2,2-trifluoroethanol (0.19 mL, 2.6 mmol) and potassium tert-butoxide (1M solution in THF, 2.5 mL, 2.5 mmol) added at 0-5° C. The resulting mixture was stirred at ambient temperature for 1 hour. Water was added (20 mL) followed by extraction with ethyl acetate (2×20 mL). The organic layer was dried over sodium sulphate and concentrated in vacuum affording 6-(2,2,2-trifluoroethoxy)nicotinonitrile, 0.42 g (96%). $^1$H NMR (400 MHz, DMSO-d$_6$) δ ppm 8.76 (d, J=2.26 Hz, 1 H) 8.28 (dd, J=8.53, 2.26 Hz, 1 H) 7.21 (d, J=8.78 Hz, 1 H) 5.09 (q, J=8.95 Hz, 2 H).

B. To 6-(2,2,2-trifluoroethoxy)nicotinonitrile (0.42 g, 2.1 mmol) in THF (4 mL) methyl magnesium bromide (3M in diethyl ether, 1.4 mL, 4.2 mmol) was added drowise at –78° C.

The reaction mixture was stirred at ambient temperature for 3-5 hours then cooled to –78° C. Methanol (10 mL) was added followed by addition of sodium borohydride (0.24 g, 6.3 mmol) and the reaction mixture was stirred at ambient temperature overnight. The mixture was diluted with water (20 mL), concentrated and extracted with chloroform (40 mL). The mixture was filtered to facilitate separation of the layers. The organic phase was separated and extracted with hydrochloric acid (5%, 20 mL). The aqueous phase was concentrated to dryness in vacuum and coevaporated twice with acetonitrile to yield the title product as a salt with hydrochloric acid (0.4 g, 75%). It was converted into the neutral form of 1-[6-(2,2,2-trifluoroethoxy)pyridin-3-yl]ethanamine by extraction with chloroform from a basicified (pH 8-9) water solution. $^1$H NMR (400 MHz, DMSO-d$_6$) δ ppm 8.13 (d, J=2.26 Hz, 1 H) 7.81 (dd, J=8.53, 2.51 Hz, 1 H) 6.91 (d, J=8.28 Hz, 1 H) 4.96 (q, J=9.29 Hz, 2 H) 4.00 (q, J=6.53 Hz, 1 H) 1.24 (d, J=6.53 Hz, 3 H). MS (ESI) m/z: 221 [M+H]

8) 1-[6-(2-fluoroethoxy)pyridin-3-yl]ethanamine

The title compound was synthesised according to the 2-step procedure described for the synthesis of 1-[6-(2,2,2- trifluoroethoxy)pyridin-3-yl]ethanamine starting from 6-chloronicotinonitrile and 2-fluoroethanol.

6-(2-fluoroethoxy)nicotinonitrile $^1$H NMR (400 MHz, DMSO-d$_6$) δ ppm 8.70 (d, J=2.51 Hz, 1 H) 8.18 (dd, J=8.66, 2.38 Hz, 1 H) 7.07 (d, J=8.78 Hz, 1 H) 4.49-4.88 (m, 4 H). MS (ESI) m/z: 167 [M+H]

1-[6-(2-fluoroethoxy)pyridin-3-yl]ethanamine $^1$H NMR (400 MHz, DMSO-d$_6$) δ ppm 8.08 (d, J=2.26 Hz, 1 H) 7.74 (dd, J=8.53, 2.51 Hz, 1 H) 6.80 (d, J=8.53 Hz, 1 H) 4.37-4.81 (m, 4 H) 3.97 (q, J=6.53 Hz, 1 H) 1.24 (d, J=6.53 Hz, 3 H). MS (ESI) m/z: 185 [M+H]

9) 1-[6-(2,2-difluoroethoxy)pyridin-3-yl]ethanamine

The title compound was synthesised according to the 2-step procedure described for the synthesis of 1-[6-(2,2,2-trifluoroethoxy)pyridin-3-yl]ethanamine starting from 6-chloronicotinonitrile and 2,2-difluoroethanol.

6-(2,2-difluoroethoxy)nicotinonitrile: $^1$H NMR (400 MHz, DMSO-d$_6$) δ ppm 8.73 (d, J=2.51 Hz, 1 H) 8.23 (dd, J=8.78, 2.51 Hz, 1 H) 7.14 (dd, J=8.66, 0.63 Hz, 1 H) 6.23-6.62 (m, 1 H) 4.58-4.74 (m, 2 H)

1-[6-(2,2-difluoroethoxy)pyridin-3-yl]ethanamine: $^1$H NMR (400 MHz, DMSO-d$_6$) δ ppm 8.11 (d, J=2.51 Hz, 1 H) 7.77 (dd, J=8.53, 2.51 Hz, 1 H) 6.85 (d, J=8.53 Hz, 1 H) 6.19-6.54 (m, 1 H) 4.46-4.60 (m, 2 H) 3.99 (q, J=6.53 Hz, 1 H) 1.24 (d, J=6.53 Hz, 3 H) MS (ESI) m/z: 203 [M+H]

10) 1-[6-(2,2,3,3-tetrafluoropoxy)pyridin-3-yl]ethanamine

The title compound was synthesised according to the 2-step procedure described for the synthesis of 1-[6-(2,2,2-trifluoroethoxy)pyridin-3-yl]ethanamine starting from 6-chloronicotinonitrile and 2,2,3,3-tetrafluoropropan-1-ol.

6-(2,2,3,3-tetrafluoropropoxy)nicotinonitrile: $^1$H NMR (400 MHz, DMSO-d$_6$) δ ppm 8.75 (d, J=2.26 Hz, 1 H) 8.26 (dd, J=8.53, 2.26 Hz, 1 H) 7.17 (d, J=8.78 Hz, 1 H) 6.51-6.84 (m, 1 H) 4.96 (t, J=14.18 Hz, 2 H)

1-[6-(2,2,3,3-tetrafluoropropoxy)pyridin-3-yl]ethanamine: $^1$H NMR (400 MHz, DMSO-d$_6$) δ ppm 8.12 (d, J=2.51 Hz, 1 H) 7.80 (dd, J=8.53, 2.51 Hz, 1 H) 6.88 (d, J=8.53 Hz, 1 H) 6.48-6.82 (m, 1 H) 4.82 (t, J=14.30 Hz, 2 H) 3.99 (q, J=6.61 Hz, 1 H) 1.24 (d, J=6.78 Hz, 3 H). MS (ESI) m/z: 253 [M+H]

11) 1-[6-(cyclopentyloxy)pyridin-3-yl]ethanamine

The title compound was synthesised according to the 2-step procedure described for the synthesis of 1-[6-(2,2,2-trifluoroethoxy)pyridin-3-yl]ethanamine starting from 6-chloronicotinonitrile and cyclopentanol.

6-(cyclopentyloxy)nicotinonitrile: $^1$H NMR (400 MHz, DMSO-d$_6$) δ ppm 8.67 (d, J=1.76 Hz, 1 H) 8.11 (dd, J=8.78, 2.26 Hz, 1 H) 6.93 (d, J=9.29 Hz, 1 H) 5.37-5.48 (m, 1 H) 1.84-2.05 (m, 2 H) 1.51-1.81 (m, 6 H). MS (ESI) m/z: 189 [M+H]

1-[6-(cyclopentyloxy)pyridin-3-yl]ethanamine: $^1$H NMR (400 MHz, DMSO-d$_6$) δ ppm 8.06 (d, J=2.51 Hz, 1 H) 7.67 (dd, J=8.53, 2.51 Hz, 1 H) 6.67 (d, J=8.53 Hz, 1 H) 5.27-5.36 (m, 1 H) 3.95 (q, J=6.53 Hz, 1 H) 1.85-2.00 (m, 2 H) 1.53-1.77 (m, 6 H) 1.23 (d, J=6.78 Hz, 3 H). MS (ESI) m/z: 207 [M+H]

12) 1-[4-(2,2,2-trifluoroethoxy)phenyl]ethanamine

The title compound was synthesised according to the procedure described for the synthesis of 1-[6-(2,2,2-trifluoroethoxy)pyridin-3-yl]ethanamine, step B, starting from 4-(2,2,2-trifluoroethoxy)benzonitrile. $^1$H NMR (400 MHz, DMSO-d$_6$) δ ppm 7.28-7.34 (m, 2 H) 6.94-7.00 (m, 2 H) 4.70 (q, J=8.78 Hz, 2 H) 3.95 (q, J=6.53 Hz, 1 H) 1.21 (d, J=6.78 Hz, 3 H). MS (ESI) m/z: 220 [M+H]

14) 1-[4-[(1-Methylpiperidin-4-yl)oxy]-3-(trifluoromethyl)phenyl]ethanamine

A. 4-[(1-Methylpiperidin-4-yl)oxy]-3-(trifluoromethyl)benzonitrile

A mixture of 4-hydroxy-N-methylpiperidine (133 mg, 1.15 mmol) and potassium tert-butoxide (150 mg, 1.27 mmol) in tetrahydrofuran (2.5 mL) was stirred under nitrogen for 10 min. 4-Fluoro-3-(trifluoromethyl)benzonitrile (218 mg, 1.15 mmol) was added, and the reaction mixture was stirred at ambient temperature for 1 h. The solvent was removed in vacuo, and the residue was partitioned between a 1 M NaOH solution and ethyl acetate. The organic layer was dried (Na$_2$SO$_4$) and evaporated. The residue was purified by column chromatography on silica gel (eluent: CHCl$_3$/MeOH/conc. NH$_3$, 95:5:0.5) affording 0.18 g (54% yield) of the pure product as a colourless solid. MS (APCI) m/z 285 [M+H]. $^1$H NMR (400 MHz, DMSO-D6) δ ppm 1.67-1.74 (m, 2 H), 1.89-1.95 (m, 2 H), 2.16 (s, 3 H), 2.26-2.31 (m, 2 H), 2.44-2.48 (m, 2 H), 4.78-4.82 (m, 1 H), 7.51 (d, J=8.8 Hz, 1 H), 8.08 (dd, J=8.8, 2.0 Hz, 1 H), 8.14 (d, J=2.0 Hz, 1 H).

B. The title compound was synthesized according to the procedure described for the synthesis of 1-[6-(2,2,2-trifluoroethoxy)pyridin-3-yl]ethanamine, step B, starting from 4-[(1-methylpiperidin-4-yl)oxy]-3-(trifluoromethyl)benzonitrile. Yield 49 mg, 62% (oil) after column chromatography on silica gel (eluent: CHCl$_3$/MeOH/conc.NH$_3$, 80:20:1). MS (APCI) m/z 303 [M+H]. $^1$H NMR (400 MHz, DMSO-D6) δ ppm 1.23 (d, J=6.5 Hz, 3 H), 1.64-1.72 (m, 2 H), 1.86-1.92 (m, 2 H), 2.17 (s, 3 H), 2.21-2.27 (m, 2 H), 2.47-2.55 (m, partly overlapped with DMSO peaks, 2 H), 3.97-4.02 (m, 1 H), 4.55-4.60 (m, 1 H), 7.21 (d, J=8.9 Hz, 1 H), 7.55 (dd, J=8.7, 1.9 Hz, 1 H), 7.60 (d, J=2.0 Hz, 1 H).

15) 1-[4-{[(2S)-2-Methoxypropyl]oxy}-3-(trifluoromethyl)phenyl]ethanamine

The title compound was synthesized according to the procedure described for the synthesis of 1-[4-[(1-methylpiperidin-4-yl)oxy]-3-(trifluoromethyl)phenyl]ethanamine, part A and B, starting from 4-fluoro-3-(trifluoromethyl)benzonitrile and (S)-(+)-2-methoxypropanol.

Yield 39 mg, 30% (oil) after column chromatography on silica gel (eluent:

CHCl$_3$/MeOH/conc.NH$_3$, 92:8:0.5). MS (APCI) m/z 278 [M+H]. $^1$H NMR (400 MHz, DMSO-D6) δ ppm 1.18 (d, J=6.5 Hz, 3 H), 1.22 (d, J=6.5 Hz, 3 H), 3.32 (s, overlapped with water peak, 3 H), 3.62-3.68 (m, 1 H), 3.98-4.08 (m, 3 H), 7.18 (d, J=8.5 Hz, 1 H), 7.55-7.58 (m, 1 H), 7.60-7.61 (m, 1 H).

16) 1-(4-{[(2S)-2-methoxypropyl]oxy}phenyl)ethanamine

A. tert-butyl [1-(4-hydroxyphenyl)ethyl]carbamate

To 1-(4-hydroxyphenyl)ethanamine (0.96 g, 7.0 mmol) in THF (20 mL) triethylamine (2.9 mL, 21 mmol) was added followed by the addition of di-tert-butyl dicarbonate (1.8 g, 8.4 mmol) in THF (20 mL) during 5 minutes. The resulting mixture was stirred for 15 hours, the volatiles removed under reduced pressure and the residue purified by silica gel column chromatography using a gradient of heptanes:ethyl acetate 9:1 to 1:1 affording 1.1 g of the tert-butyl [1-(4-hydroxyphenyl)ethyl]carbamate (64%). $^1$H NMR (400 MHz, DMSO-d$_6$) δ ppm 9.18 (s, 1 H) 7.18 (d, J=7.78 Hz, 1 H) 7.03-7.11 (m, J=8.41 Hz, 2 H) 6.63-6.72 (m, 2 H) 4.45-4.56 (m, 1 H) 1.35 (s, 9 H) 1.25 (d, J=7.03 Hz, 3 H)

MS (ESI) m/z: 238 [M+H]

B. tert-butyl [1-(4-{[(2S)-2-methoxypropyl]oxy}phenyl)ethyl]carbamate

To tert-butyl [1-(4-hydroxyphenyl)ethyl]carbamate (0.31 g, 1.3 mmol) in THF (10 mL) (s)-(+)-2-methoxypropanol (0.14 g, 1.5 mmol), triphenylphosphine (0.36 g, 1.4 mmol) and diisopropyl azodicarboxylate (0.27 mL, 1.4 mmol) were added; the resulting reaction mixture stirred at ambient temperature for 21 hours. The volatiles were removed under reduced pressure and the residue purified on silica gel column chromatography using heptanes:ethyl acetate 4:1 affording 0.29 g of tert-butyl [1-(4-{[(2S)-2-methoxypropyl]oxy}phenyl)ethyl]carbamate (74%). $^1$H NMR (400 MHz, DMSO-$d_6$) δ ppm 7.29 (d, J=8.28 Hz, 1 H) 7.15-7.21 (m, J=8.78 Hz, 2 H) 6.84-6.89 (m, J=8.53 Hz, 2 H) 4.50-4.60 (m, 1 H) 3.84-3.93 (m, 2 H) 3.59-3.68 (m, 1 H) 3.30 (s, 3 H) 1.35 (s, 9 H) 1.26 (d, J=7.03 Hz, 3 H) 1.15 (d, J=6.53 Hz, 3 H). MS (ESI) m/z: 310 [M+H]

C. 1-(4-{[(2S)-2-methoxypropyl]oxy}phenyl)ethanamine tert-Butyl [1-(4-{[(2S)-2-methoxypropyl]oxy}phenyl)ethyl]carbamate (0.29 g, 0.94 mmol) was treated with trifluoroacetic acid (2 mL) in dichloromethane (18 mL) for 25 minutes, the volatiles removed under reduced pressure and the residue purified by silica gel column chromatography using dichloromethane:methanol:triethylamine 98:1:1 giving the title compound in 0.12 g (59%) yield $^1$H NMR (400 MHz, DMSO-$d_6$) δ ppm 8.14 (s, 2 H) 7.34-7.41 (m, J=8.78 Hz, 2 H) 6.97-7.03 (m, 2 H) 4.35 (q, J=6.78 Hz, 1 H) 3.93 (d, J=5.02 Hz, 2 H) 3.60-3.70 (m, 1 H) 3.30 (s, 3 H) 2.96 (q, J=7.11 Hz, 1 H) 1.45 (d, J=6.78 Hz, 3 H) 1.16 (d, J=6.27 Hz, 3 H)

Syntheses of the intermediates: amines, 19)-20)

19) [(5-tert-butyl-2-thienyl)ethyl]amine

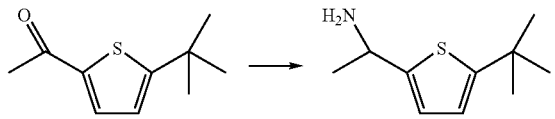

1-(5-tert-butyl-2-thienyl)ethanone (410 mg, 2.2 mmol) and Ti(OiPr)$_4$ (128 mg, 4.5 mmol) are stirred overnight in 2 N NH$_3$ in ethanol (5.5 ml, 11 mmol). To this paste is added NaBH$_4$ (124 mg, 3.3 mmol) and stirring is continued for a further 24 hrs. The reaction is then diluted with NH$_4$OH and stirred for 1 hour. The mixture is filtered through celite and rinsed with ethyl acetate. Water and ethyl acetate are added and the organic layer is separated. The aqueous layer is extracted three times with ethyl acetate and the combined organics are washed with 1 N HCl. The aqueous phase is separated and washed with ethyl acetate, made basic with 1 N NaOH then extracted three times with ethyl acetate. The combined organic layers are then dried with over MgSO$_4$, filtered and concentrated.

Yielded 171 mg, 42%.

$^1$H NMR (400 MHz, CDCl$_3$) δ ppm 1.37 (s, 9 H), 1.47 (d, J=6.64 Hz, 3 H), 4.29 (q, J=6.64, 1H), 6.64 (d, J=3.52 Hz, 1 H), 6.69 (dd, J=3.52, 0.59 Hz, 1 H).

20 [1-(5-tert-butylpyridin-2-yl)ethyl]amine

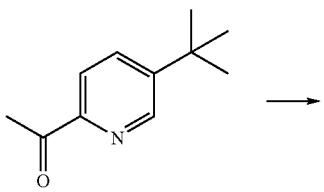

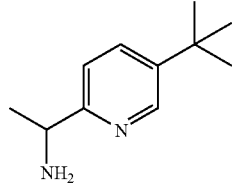

1-(5-tert-butylpyridin-2-yl)ethanone (2.2 mmol) and Ti(O-iPr)$_4$ (128 mg, 4.5 mmol) are stirred overnight in 2 N NH$_3$ in ethanol (5.5 ml, 11 mmol). To this paste is added NaBH$_4$ (124 mg, 3.3 mmol) and stirring is continued for a further 24 hrs. The reaction is then diluted with NH$_4$OH and stirred for 1 hour. The mixture is filtered through celite and rinsed with ethyl acetate. Water and ethyl acetate are added and the organic layer is separated. The aqueous layer is extracted three times with ethyl acetate and the combined organics are washed with 1 N HCl. The aqueous phase is separated and washed with ethyl acetate, made basic with 1 N NaOH then extracted three times with ethyl acetate. The combined organic layers are then dried with over MgSO$_4$, filtered and concentrated.

Syntheses of the Intermediates: nicotinonitriles, 21)-24)

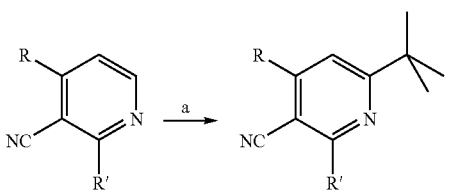

Intermediate 21: R=H, R'=H
Intermediate 22: R=H, R'=Cl
Intermediate 23: R=H, R'=OCH$_3$
Intermediate 24: R=CH$_3$, R'=H
a) (CH$_3$)$_3$CO$_3$H, AgNO$_3$, H$_2$SO$_3$ (NH$_4$)S$_2$O$_4$
21) 6-tert-butylnicotinonitrile Pivalic acid (144 mol, 5 eq) and AgNO$_3$ (3.76 mmol, 0.13 eq) are added to a suspension of the 3-cyanopyridine (29 mmol, 1 eq) in 40 ml H$_2$O. The mixture is stirred for 20 min after which is added 60 ml of a 10% H$_2$SO$_4$ solution. The reaction is stirred for a further 20 min then heated to 70° C. An aqueous solution of (NH$_4$)$_2$S$_2$O$_8$ (8.6 mmol, 1.3 eq) is added dropwise over 30 minutes and the heating is continued for 2 hours or until completion by TLC. After cooling the in ice, 2 N NaOH is added and the reaction is extracted 3 times with ethyl acetate, dried over Na$_2$SO$_4$, filtered and concentration. Purification is performed on silica gel with ethyl acetate/hexanes.

22) 6-tert-butyl-2-chloronicotinonitrile

The title compound was synthesized according to the procedure described for the synthesis of 6-tert-butylnicotinonitrile starting from 2-chloronicotinonitrile (3.91 g, 28 mmol), pivalic acid (14.4 g, 141 mmol), AgNO$_3$ (0.622 g, 3.66 mmol), (NH$_4$)$_2$S$_2$O$_8$ (8.36 g, 36.6 mmol) and 50 ml 10% H$_2$SO$_4$. Purified by normal phase chromatography using 100 heptane to 95/5 heptane/ethyl acetate. (Yield: 42%, 2.3 g). $^1$H NMR (400 MHz, CDCl$_3$) δ ppm 1.34 (s, 9 H), 7.36 (d, J=8.20 Hz, 1 H), 7.88 (d, J=8.20 Hz, 1 H).

23) 6-tert-butyl-2-methoxynicotinonitrile

The title compound was synthesized according to the procedure described for the synthesis of 6-tert-butylnicotinonitrile starting from 2-methoxynicotinonitrile (8.02 g, 5.98 mmol), pivalic acid (3.05 g, 39.9 mmol), AgNO₃ (0.13 g, 0.78 mmol), (NH₄)₂S₂O₈ (1.78 g, 7.78 mmol) and 6 ml 10% H₂SO₄. Purified by normal phase chromatography using 95/5 to 90/10 heptane/ethyl acetate. (Yield: 80 mg, 7%). $^1$H NMR (400 MHz, CDCl₃) δ ppm 1.33 (s, 9 H), 4.04 (s, 3 H), 6.97 (d, J=7.81 Hz, 2 H), 7.78 (d, J=7.81 Hz, 2 H).

Intermediate 23 was also prepared by microwaving intermediate 22 (100 mg, 0.5 mmol) in the presence of K₂CO₃ (140 mg, 1.02 mmol) in 1.5 ml of MeOH at 160° C. for 30 min.

(Yield: 68 mg, 72%)

24) 6-tert-butyl-4-methylnicotinonitrile

The title compound was synthesized according to the procedure described for the synthesis of 6-tert-butylnicotinonitrile starting from 4-methylnicotinonitrile (0.5 g, 4.23 mmol), pivalic acid (2.2 g, 21.1 mmol), AgNO₃ (0.09 g, 0.55 mmol), (NH₄)₂S₂O₈ (1.25 g, 5.5 mmol) and 7.5 ml 10% H₂SO₄. Purified by normal phase chromatography using 95/5 to 90/10 heptane/ethyl acetate. (Yield: 578 mg, 78%). $^1$H NMR (400 MHz, CDCl₃) δ ppm 1.36 (s, 9 H), 2.53 (s, 3 H), 7.28 (s, 1 H), 8.72 (s, 1 H).

Syntheses of the Intermediates: amines, 25)-28)

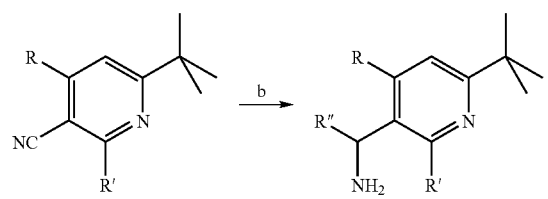

Intermediate 25: R=H, R'=H, R"=CH₃
Intermediate 26: R=H, R'=Cl, R"=CH₃
Intermediate 27: R=H, R'=OCH₃, R"=CH₃
Intermediate 28: R=CH₃, R'=H, R"=CH₃
b) 1.4 M MeMgBr 75/25 toluene/THF, NaBH₄

25) [1-(6-tert-butylpyridin-3-yl)ethyl]amine

A solution of MeMgBr 1.4 M 75/25 toluene/THF (8.9 ml, 12.48 mmol) is added dropwise over 5 min to an ice cooled solution of 6-tert-butylnicotinonitrile (intermediate 21) (1 g, 6.24 mmol) in 15 mL of THF. The reaction is stirred for 6 hr and cooled with a dry ice bath. MeOH is then added dropwise followed by the incremental addition of NaBH₄ (0.59 g, 15.9 mmol). The reaction is stirred over night, water and CH₂Cl₂ are then added and the resulting paste is filtered through celite and rinsed with CH₂Cl₂. The reaction is concentrated to remove the organics and extracted 3 times with ethyl acetate. The combined organic layers are extracted with 1H HCl. The aqueous layer is basified with 28% NH₄OH and extracted 3 times with ethyl acetate. The combined organic layers are washed with brine, dried over Na₂SO₄, filtered and concentrated. (Yield: 488 mg, 49%). $^1$H NMR (400 MHz, CDCl₃) δ ppm 1.36 (s, 9 H) 1.40 (d, J=6.60 Hz, 3 H) 4.15 (q, J=6.60 Hz, 1 H) 7.31 (d, J=8.20 Hz, 1 H) 7.63 (dd, J=8.20, 2.34 Hz, 1 H) 8.52 (d, J=2.34 Hz, 1 H).

26) [1-(6-tert-butyl-2-chloropyridin-3-yl)ethyl]amine

The title compound was synthesized according to the procedure described for the synthesis of [1-(6-tert-butylpyridin-3-yl)ethyl]amine starting from 6-tert-butyl-2-chloronicotinonitrile (intermediate 22) (2.0 g, 10.3 mmol), MeMgBr (18 ml, 25.7 mmol) and NaBH₄ (970 mg, 25.7 mmol). The resulting material was used crude in the following coupling step.

(Yield: 1.76 g, 79%) $^1$H NMR (400 MHz, CDCl₃) δ ppm 1.34 (s, 9 H) 1.39 (d, J=6.64 Hz, 3 H) 4.47 (q, J=6.64 Hz, 1 H) 7.26 (d, J=8.01 Hz, 1 H) 7.78 (d, J=8.01 Hz, 1 H).

27) [1-(6-tert-butyl-2-methoxypyridin-3-yl)ethyl]amine

The title compound was synthesized according to the procedure described for the synthesis of [1-(6-tert-butylpyridin-3-yl)ethyl]amine starting from 6-tert-butyl-2-methoxynicotinonitrile (intermediate 23) (66 mg, 0.347 mmol), MeMgBr 1.4 M 75/25 toluene/THF (743 µL, 1.04 mmol) and NaBH₄ (32.8 mg, 0.87 mmol. Material isolated from the workup was used without further purification in the preparation.

28) [1-(6-tert-butyl-4-methylpyridin-3-yl)ethyl]amine

The title compound was synthesized according to the procedure described for the synthesis of [1-(6-tert-butylpyridin-3-yl)ethyl]amines starting from 6-tert-butyl-4-methylnicotinonitrile (intermediate 24) (250 mg, 1.43 mmol), MeMgBr 1.4 M 75/25 toluene/THF (2.55 ml, 3.58 mmol) and NaBH₄ (135 mg, 3.58 mmol). Purified by normal phase chromatography with 15 to 20% MeOH/CH₂Cl₂. (Yield 55 mg, 20%). $^1$H NMR (400 MHz, CDCl₃) δ ppm 1.34 (s, 9 H) 1.42 (d, J=6.64 Hz, 3 H) 2.35 (s, 3 H) 4.34 (q, J=6.64 Hz, 1 H) 7.07 (s, 1 H) 8.60 (s, 1 H).

Syntheses of the Intermediates: amines, 29)-32)

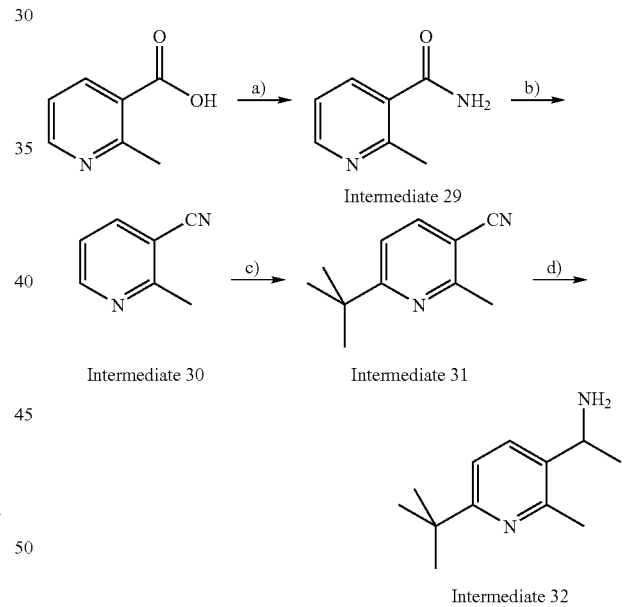

a) HATU, DIPEA, NH₃(g), DMF b) cyanuric chloride c) (CH₃)₃CO₃H, AgNO₃, H₂SO₃ (NH₄)S₂O₄ d) 1.4 M MeMgBr 75/25 toluene/THF, NaBH₄

29) 2-methylnicotinamide

To a solution of 2-methylnicotinic acid (0.537 mg, 3.9 mmol) in 20 mL of DMF at 0° C. was added HATU (1.56 g, 4.1 mmol) followed by the dropwise addition of DIPEA (0.72 ml, 4.1 mmol). NH₃(g) was then bubbled into the solution for 15 mins. The reaction was allowed to stir overnight. The resulting paste was filtered and rinsed with cold DMF and discarded. The mother liquor was concentrated and purified by normal phase chromatography using CH₂Cl₂/7 N NH₃ in MeOH: 93/7 as eluent. Yielded a white solid (405 mg, 76%).

¹H NMR (400 MHz, CHLOROFORM-D) δ ppm 1.34 (s, 9 H), 1.36 (d, J=6.64 Hz, 3H), 2.56 (s, 3 H), 4.32-4.40 (m, 1 H), 7.15-7.19 (m, J=8.20 Hz, 1 H), 7.68 (d, J=8.20 Hz, 1 H)

30) 2-methyl-nicotinonitrile

Cyanuric acid (418 mg, 2.2 mmol) was added in one portion to a suspension of 2-methyl-nicotinamide (intermediate 29) (613 mg, 4.5 mmol) in 2.5 ml of DMF cooled in ice. The reaction was stirred for 2.5 hours then poured into ice. The reaction was extracted with ethyl acetate until the organic layer no longer contained product. The combined organic layers, were dried over $Na_2SO_4$, filtered and concentrated. Purified on normal phase chromatography with ethyl acetate/heptane 0 to 50 gradient then 50/50 EA/heptane. Yield (216 mg, 41%). ¹H NMR (400 MHz, CHLOROFORM-D) δ ppm 2.78 (s, 3 H), 7.25 (dd, J=7.71, 4.98 Hz, 1 H), 7.89 (dd, J=7.81, 1.56 Hz, 1 H), 8.68 (s, 1 H)

31) 6-tert-butyl-2-methylnicotinonitrile

The title compound was synthesized according to the procedure described for the synthesis of 6-tert-butylnicotinonitrile starting from 2-methyl-nicotinonitrile (intermediate 30) (216 mg, 1.7 mmol), pivalic acid (868 mg, 8.5 mmol), $AgNO_3$ (38.5 mg, 0.23 mmol), $(NH_4)_2S_2O_8$ (504 mg, 2.2 mmol) and 3.75 ml 10% $H_2SO_4$. Purification by normal phase chromatography with 100% heptane to 90/10 Heptane/EA yielded 240 mg of a mixture of both mono and di-t-butylated pyridines. Material used crude in the preparation of [1-(6-tert-butyl-2-methylpyridin-3-yl)ethyl]amine (intermediate 32) below.

32) [1-(6-tert-butyl-2-methylpyridin-3-yl)ethyl]amine

The title compound was synthesized according to the procedure described for the synthesis of 6-tert-butylnicotinonitrile starting from 6-tert-butyl-2-methylnicotinonitrile (intermediate 31) (100 mg, 0.57 mmol), used crude from the above described description; MeMgBr 1.4 M 75/25 toluene/THF (1.4 ml, 1.4 mmol) and $NaBH_4$ (55 mg, 1.4 mmol). Purified by normal phase chromatography with 20% MeOH/$CH_2Cl_2$. (Yield 31.5 mg, 29%). ¹H NMR (400 MHz, CHLOROFORM-D) δ ppm 1.34 (s, 9 H), 1.36 (d, J=6.64 Hz, 3 H), 2.56 (s, 3 H), 4.32-4.40 (m, 1 H), 7.15-7.19 (m, J=8.20 Hz, 1 H), 7.68 (d, J=8.20 Hz, 1 H).

Synthesis of the Target Compounds

General Method 1.

To N-[(1S)-1-(4-hydroxyphenyl)ethyl]-2-(7-nitro-1H-benzimidazol-1-yl)acetamide (0.25 g, 0.73 mmol) in THF (10 mL) an appropriate commercially available alcohol (0.88 mmol) and triphenylphosphine (0.21 g, 0.80 mmol) were added followed by addition of diisopropyl azodicarboxylate (160 mL, 0.80 mmol). The reaction mixture was stirred at ambient temperature for 18 hours and the volatiles were removed. The crude product was purified using reversed phase preparative HPLC.

General Method 2.

To a solution of a 7-substituted (1H-benzimidazol-1-yl) acetic acid, prepared as described above (0.14 mmol), triethylamine (0.04 mL, 0.28 mmol) and an appropriate amine (commercially available or described in the literature or described above, 0.15 mmol) in acetonitrile (1 ml) O-(7-azabenzotriazol-1-yl)-N,N,N'-tetramethyluronium hexafluorophosphate (80 mg, 0.21 mmol) was added. The reaction mixture was stirred at ambient temperature for 0.5-3 h. The mixture was quenched with methanol and the volatiles were removed in vacuo.

In Examples 7-51, the crude material was purified by preparative HPLC on XTerra $C_8$ column (19×300 mm) using a gradient of 0.1 M aqueous ammonium acetate in acetonitrile as an eluent.

In Examples 52-76, the crude material was purified by preparative HPLC on a Phenomenex, Synersi 4µ Polar RP (or Gemini 5 µC18) column using a gradient of 0.05% aqueous trifluoroacetic acid and acetonitrile as an eluent (or aqueous amonium bicarbonate 10 mM and acetonitrile depending on the best pH conditions for separation).

The compounds in Table 1 below were synthesised according to General method 1

TABLE 1

| Ex. # | Name | MW found [M + H] | ¹H NMR | Starting material |
|---|---|---|---|---|
| 1 | N-[(1S)-1-(4-isopropoxyphenyl)-ethyl]-2-(7-nitro-1H-benzimidazol-1-yl)acetamide | 383.3 | (400 MHz, DMSO-d6) δ ppm 8.61 (d, J = 7.83 Hz, 1H) 8.40 (s, 1H) 8.10 (dd, J = 7.96, 0.88 Hz, 1H) 7.98 (d, J = 8.08 Hz, 1H) 7.39 (t, J = 7.96 Hz, 1H) 7.16-7.25 (m, 2H) 6.81-6.88 (m, 2H) 5.20 (s, 2H) 4.74-4.84 (m, 1H) 4.52-4.63 (m, 1H) 1.34 (d, J = 7.07 Hz, 3H) 1.25 (d, J = 6.06 Hz, 6H) | propan-2-ol |
| 2 | N-((1S)-1-{4-[2-fluoro-1-(fluoromethyl)ethoxy]phenyl}-ethyl)-2-(7-nitro-1H-benzimidazol-1-yl)acetamide | 419.0 | (400 MHz, DMSO-d6) δ ppm 8.64 (d, J = 7.83 Hz, 1H) 8.40 (s, 1H) 8.10 (d, J = 7.07 Hz, 1H) 7.98 (d, J = 7.33 Hz, 1H) 7.39 (t, J = 8.08 Hz, 1H) 7.21-7.29 (m, 2H) 6.95-7.02 (m, 2H) 5.21 (s, 2H) 4.54-4.98 (m, 6H) 1.35 (d, J = 7.07 Hz, 3H) | 1,3-difluoropropan-2-ol |
| 3 | N-{(1S)-1-[4-(2-fluoroethoxy)phenyl]ethyl}-2-(7-nitro-1H-benzimidazol-1-yl)acetamide | 387 | (400 MHz, DMSO-d6) δ ppm 8.66 (d, J = 8.08 Hz, 1H) 8.41 (s, 1H) 8.10 (dd, J = 8.08, 1.01 Hz, 1H) 7.98 (dd, J = 8.08, 0.76 Hz, 1H) 7.39 (t, J = 7.96 Hz, 1H) 7.20-7.28 (m, 2H) 6.87-6.95 (m, 2H) 5.21 (s, 2H) | 2-fluoroethanol |

TABLE 1-continued

| Ex. # | Name | MW found [M + H] | ¹H NMR | Starting material |
|---|---|---|---|---|
| 4 | N-((1S)-1-{4-[(1-methylprop-2-yn-1-yl)oxy]phenyl}ethyl)-2-(7-nitro-1H-benzimidazol-1-yl)acetamide | 393.0 | 4.63-4.86 (m, 3H) 4.14-4.28 (m, 2H) 1.35 (d, J = 6.82 Hz, 3H) (400 MHz, DMSO-d6) δ ppm 8.63 (d, J = 8.08 Hz, 1H) 8.40 (s, 1H) 8.10 (dd, J = 8.08, 1.01 Hz, 2H) 7.98 (dd, J = 8.08, 0.76 Hz, 1H) 7.40 (t, J = 7.96 Hz, 1H) 7.19-7.28 (m, 2H) 6.90-6.98 (m, 2H) 5.21 (s, 2H) 5.02-5.11 (m, 1H) 4.75-4.87 (m, 1H) 3.47-3.52 (m, 1H) 1.54 (d, J = 6.57 Hz, 3H) 1.35 (d, J = 6.82 Hz, 3H) | but-3-yn-2-ol |
| 5 | N-{(1S)-1-[4-(2-methoxy-1-methylethoxy)-phenyl]ethyl}-2-(7-nitro-1H-benzimidazol-1-yl)acetamide | 413 | (400 MHz, CD₃OD) δ ppm 8.29 (s, 1H) 8.05 (d, J = 8.08 Hz, 2H) 7.42 (t, J = 8.08 Hz, 1H) 7.21-7.28 (m, 2H) 6.86-6.93 (m, 2H) 5.24-5.35 (m, 2H) 4.90 (q, J = 6.99 Hz, 1H) 4.51-4.61 (m, 1H) 3.45-3.59 (m, 2H) 3.38 (s, 3H) 1.46 (d, J = 6.82 Hz, 3H) 1.26 (d, J = 6.06 Hz, 3H) | 1-methoxypropan-2-ol |
| 6 | N-[(1S)-1-(4-ethoxy-phenyl)ethyl]-2-(7-nitro-1H-benzimidazol-1-yl)acetamide | 369.0 | (400 MHz, DMSO-d6) δ ppm 8.61 (d, J = 8.08 Hz, 1H) 8.40 (s, 1H) 8.10 (dd, J = 7.96, 0.88 Hz, 1H) 7.95-8.01 (m, 1H) 7.39 (t, J = 7.96 Hz, 1H) 7.18-7.25 (m, 2H) 6.82-6.90 (m, 2H) 5.20 (s, 2H) 4.74-4.85 (m, 1H) 4.00 (q, J = 6.91 Hz, 2H) 1.25-1.39 (m, 6H) | ethanol |

The compounds in Table 2 below were synthesised according to General method 2

TABLE 2

| Ex. # | Name | MW found [M + H] | ¹H NMR | Starting material |
|---|---|---|---|---|
| 7 | 2-(7-nitro-1H-benzimidazol-1-yl)-N-{1-[6-(2,2,2-trifluoroethoxy)pyridin-3-yl]ethyl}acetamide | 424.0 | (400 MHz, DMSO-d6) δ ppm 8.77 (d, J = 7.58 Hz, 1H) 8.40 (s, 1H) 8.07-8.16 (m, 2H) 7.97 (dd, J = 8.08, 0.76 Hz, 1H) 7.75 (dd, J = 8.46, 2.40 Hz, 1H) 7.39 (t, J = 7.96 Hz, 1H) 6.96 (d, J = 8.34 Hz, 1H) 5.21 (s, 2H) 4.97 (q, J = 9.26 Hz, 2H) 4.82-4.92 (m, 1H) 1.39 (d, J = 7.07 Hz, 3H) | 1-[6-(2,2,2-trifluoroethoxy)pyridin-3-yl]ethanamine |
| 8 | 2-(7-chloro-1H-benzimidazol-1-yl)-N-{1-[6-(2,2,2-trifluoroethoxy)pyridin-3-yl]ethyl}acetamide | 413.0 | (400 MHz, DMSO-d6) δ ppm 8.80 (d, J = 7.83 Hz, 1H) 8.20 (s, 1H) 8.14 (d, J = 2.27 Hz, 1H) 7.77 (dd, J = 8.59, 2.53 Hz, 1H) 7.62 (dd, J = 7.71, 1.14 Hz, 1H) 7.14-7.25 (m, 2H) 6.97 (d, J = 8.59 Hz, 1H) 5.13-5.26 (m, 2H) 4.89-5.03 (m, 3H) 1.40 (d, J = 6.82 Hz, 3H) | 1-[6-(2,2,2-trifluoroethoxy)pyridin-3-yl]ethanamine |
| 9 | N-{1-[6-(2,2-difluoroethoxy)pyridin-3-yl]ethyl}-2-(7-nitro-1H-benzimidazol-1-yl)acetamide | 406.0 | (400 MHz, DMSO-d6) δ ppm 8.75 (d, J = 7.58 Hz, 1H) 8.40 (s, 1H) 8.07-8.16 (m, 2H) 7.97 (dd, J = 8.08, 0.76 Hz, 1H) 7.71 (dd, J = 8.59, 2.27 Hz, 1H) 7.39 (t, J = 8.08 Hz, 1H) 6.89 (d, J = 8.59 Hz, 1H) 6.21-6.55 (m, 1H) 5.21 (s, 2H) 4.80-4.91 (m, 1H) 4.45-4.61 (m, 2H) 1.38 (d, J = 7.07 Hz, 3H) | 1-[6-(2,2-difluoroethoxy)pyridin-3-yl]ethanamine |

TABLE 2-continued

| Ex. # | Name | MW found [M + H] | ¹H NMR | Starting material |
|---|---|---|---|---|
| 10 | 2-(7-nitro-1H-benzimidazol-1-yl)-N-{1-[6-(2,2,3,3-tetra-fluoropropoxy)pyridin-3-yl]ethyl}acetamide | 456.0 | (400 MHz, DMSO-d6) δ ppm 8.76 (d, J = 7.58 Hz, 1H) 8.40 (s, 1H) 8.06-8.17 (m, 2H) 7.97 (dd, J = 8.08, 0.76 Hz, 1H) 7.74 (dd, J = 8.59, 2.53 Hz, 1H) 7.39 (t, J = 7.96 Hz, 1H) 6.92 (d, J = 8.59 Hz, 1H) 6.51-6.83 (m, 1H) 5.21 (s, 2H) 4.77-4.94 (m, 3H) 1.38 (d, J = 7.07 Hz, 3H) | 1-[6-(2,2,3,3-tetrafluoropropoxy)pyridin-3-yl]ethanamine |
| 11 | 2-(7-chloro-1H-benzimidazol-1-yl)-N-{1-[6-(2,2,3,3-tetra-fluoropropoxy)pyridin-3-yl]ethyl}acetamide | 445.0 | (400 MHz, DMSO-d6) δ ppm 8.80 (d, J = 7.83 Hz, 1H) 8.20 (s, 1H) 8.14 (d, J = 2.27 Hz, 1H) 7.77 (dd, J = 8.59, 2.27 Hz, 1H) 7.62 (dd, J = 7.71, 1.14 Hz, 1H) 7.13-7.26 (m, 2H) 6.94 (d, J = 8.34 Hz, 1H) 6.50-6.84 (m, 1H) 5.13-5.26 (m, 2H) 4.89-5.01 (m, 1H) 4.83 (t, J = 14.27 Hz, 2H) 1.40 (d, J = 7.07 Hz, 3H) | 1-[6-(2,2,3,3-tetrafluoropropoxy)pyridin-3-yl]ethanamine |
| 12 | N-{1-[6-(cyclopentyloxy)pyridine-3-yl]ethyl}-2-(7-nitro-1H-benzimidazol-1-yl)acetamide | 410.0 | (400 MHz, DMSO-d6) δ ppm 8.71 (d, J = 7.58 Hz, 1H) 8.40 (s, 1H) 8.04-8.14 (m, 2H) 7.97 (dd, J = 8.08, 0.76 Hz, 1H) 7.61 (dd, J = 8.59, 2.53 Hz, 1H) 7.39 (t, J = 7.96 Hz, 1H) 6.71 (d, J = 8.59 Hz, 1H) 5.28-5.36 (m, 1H) 5.20 (s, 2H) 4.77-4.88 (m, 1H) 1.85-1.98 (m, 2H) 1.50-1.75 (m, 6H) 1.37 (d, J = 6.82 Hz, 3H) | 1-[6-(cyclopentyloxy)pyridin-3-yl]ethanamine |
| 13 | N-[1-(4-{[(2S)-2-methoxypropyl]oxy}phenyl)ethyl]-2-(7-nitro-1H-benzimidazol-1-yl)acetamide | 413.0 | (400 MHz, DMSO-d6) δ ppm 8.62 (d, J = 7.83 Hz, 1H) 8.40 (s, 1H) 8.10 (d, J = 7.83 Hz, 1H) 7.98 (d, J = 7.33 Hz, 1H) 7.39 (t, J = 8.08 Hz, 1H) 7.18-7.26 (m, J = 8.59 Hz, 2H) 6.85-6.93 (m, 2H) 5.21 (s, 2H) 4.75-4.87 (m, 1H) 3.86-3.95 (m, 2H) 3.60-3.70 (m, 1H) 3.31 (s, 3H) 1.34 (d, J = 7.07 Hz, 3H) 1.16 (d, J = 6.32 Hz, 3H) | 1-(4-{[(2S)-2-methoxypropyl]oxy}phenyl)ethanamine |
| 14 | 2-(7-nitro-1H-benzimidazol-1-yl)-N-{1-[4-(2,2,2-trifluoroethoxy)phenyl]ethyl}acetamide | 423.0 | (400 MHz, DMSO-d6) δ ppm 8.68 (d, J = 8.08 Hz, 1H) 8.41 (s, 1H) 8.10 (dd, J = 7.96, 0.88 Hz, 1H) 7.98 (dd, J = 7.96, 0.63 Hz, 1H) 7.39 (t, J = 8.08 Hz, 1H) 7.24-7.31 (m, 2H) 6.97-7.04 (m, 2H) 5.21 (s, 2H) 4.77-4.88 (m, 1H) 4.73 (q, J = 8.84 Hz, 2H) 1.35 (d, J = 7.07 Hz, 3H) | 1-[4-(2,2,2-trifluoroethoxy)phenyl]ethanamine |
| 15 | N-[(1S)-1-(4-{[(1S)-1-methylpropyl]oxy}phenyl)ethyl]-2-(7-nitro-1H-benzimidazol-1-yl)acetamide | 397.1 | (400 MHz, DMSO-d6) δ ppm 0.90 (t, J = 7.4 Hz, 3H) 1.20 (d, J = 6.0 Hz, 3H) 1.34 (d, J = 7.0 Hz, 3H) 1.49-1.66 (m, 2H) 4.28-4.38 (m, 1H) 4.72-4.83 (m, 1H) 5.19 (s, 2H) 6.82-6.86 (m, 2H) 7.14-7.23 (m, J = 8.8 Hz, 2H) 7.39 (t, J = 8.0 Hz, 1H) 7.97 (d, J = 7.8 Hz, 1H) 8.09 (d, J = 8.0 Hz, 1H) 8.39 (s, 1H) 8.60 (d, J = 8.0 Hz, 1H) | (1S)-1-(4-{[(1S)-1-methylpropyl]oxy}phenyl)ethanamine |
| 16 | N-(1-{4-[chloro(difluoro)methyl]phenyl}ethyl)-2-(7-nitro-1H-benzimidazol-1-yl)acetamide | 409.1 | (400 MHz, DMSO-d6) δ ppm 1.40 (d, J = 7.0 Hz, 3H) 4.90 (t, J = 7.3 Hz, 1H) 5.25 (s, 2H) 7.39 (t, J = 8.0 Hz, 1H) 7.51 (d, J = 8.5 Hz, 2H) 7.66 (d, J = 8.5 Hz, 2H) 7.98 (d, J = 8.0 Hz, 1H) 8.10 (dd, J = 7.9, 0.9 Hz, 1H) 8.40 (s, 1H) 8.83 (d, J = 7.8 Hz, 1H) | 1-{4-[chloro(difluoro)methyl]phenyl}ethanamine |
| 17 | 2-(7-chloro-1H-benzimidazol-1-yl)-N-(1-{4-[chloro(difluoro)methyl]phenyl}ethyl)acetamide | 398.1 | (400 MHz, DMSO-d6) δ ppm 1.41 (d, J = 7.0 Hz, 3H) 4.94-5.04 (m, 1H) 5.22 (s, 2H) 7.17 (t, J = 7.8 Hz, 1H) 7.21-7.25 (m, 1H) 7.54 (d, J = 8.3 Hz, 2H) 7.61 (dd, J = 7.8, 1.0 Hz, 1H) | 1-{4-[chloro(difluoro)methyl]phenyl}ethanamine |

TABLE 2-continued

| Ex. # | Name | MW found [M + H] | ¹H NMR | Starting material |
|---|---|---|---|---|
| 18 | 2-(7-chloro-1H-benzimidazol-1-yl)-N-{1-[4-(2,2-difluoroethoxy)phenyl]ethyl}acetamide | 394.2 | 7.67 (d, J = 8.3 Hz, 2H) 8.19 (s, 1H) 8.86 (d, J = 7.8 Hz, 1H) (400 MHz, DMSO-d6) δ ppm 1.37 (d, J = 7.0 Hz, 3H) 4.29 (td, J = 14.7, 3.5 Hz, 2H) 4.85-4.95 (m, 1H) 5.19 (s, 2H) 6.37 (tt, J = 54.5, 3.6 Hz, 1H) 6.96 (d, J = 8.8 Hz, 2H) 7.17 (t, J = 7.8 Hz, 1H) 7.21-7.25 (m, 1H) 7.26-7.31 (m, 2H) 7.62 (dd, J = 7.8, 1.00 Hz, 1H) 8.19 (s, 1H) 8.69 (d, J = 8.0 Hz, 1H) | 1-[4-(2,2-difluoroethoxy)phenyl]ethanamine |
| 19 | N-{1-[4-(2,2-difluoroethoxy)phenyl]ethyl}-2-(7-nitro-1H-benzimidazol-1-yl)acetamide | 405.2 | (400 MHz, DMSO-d6) δ ppm 1.35 (d, J = 6.8 Hz, 3H) 4.29 (td, J = 14.7, 3.6 Hz, 2H) 4.76-4.87 (m, 1H) 5.21 (s, 2H) 6.37 (tt, J = 54.6, 3.5 Hz, 1H) 6.92-6.99 (m, 2H) 7.23-7.28 (m, 2H) 7.39 (t, J = 8.0 Hz, 1H) 7.98 (d, J = 8.0 Hz, 1H) 8.10 (dd, J = 8.0, 1.0 Hz, 1H) 8.40 (s, 1H) 8.64 (d, J = 8.0 Hz, 1H) | 1-[4-(2,2-difluoroethoxy)phenyl]ethanamine |
| 20 | 2-(7-chloro-1H-benzimidazol-1-yl)-N-(1-{4-[2-fluoro-1-(fluoromethyl)ethoxy]phenyl}ethyl)acetamide | 408.2 | (400 MHz, DMSO-d6) δ ppm 1.37 (d, J = 6.8 Hz, 3H) 4.55-4.80 (m, 4H) 4.80-4.96 (m, 2H) 5.19 (s, 2H) 6.97-7.02 (m, 1H) 7.17 (t, J = 7.8 Hz, 1H) 7.20-7.24 (m, 1H) 7.24-7.29 (m, J = 8.5 Hz, 2H) 7.62 (dd, J = 7.7, 1.13 Hz, 1H) 8.19 (s, 1H) 8.68 (d, J = 7.8 Hz, 1H) | 1-{4-[2-fluoro-1-(fluoromethyl)ethoxy]phenyl}ethanamine |
| 21 | 2-(7-acetyl-1H-benzimidazol-1-yl)-N-(1-{4-[2-fluoro-1-(fluoromethyl)ethoxy]phenyl}ethyl)acetamide | 416.2 | (400 MHz, DMSO-d6) δ ppm 1.34 (d, J = 7.0 Hz, 3H) 2.44 (s, 3H) 4.54-4.78 (m, 4H) 4.78-4.96 (m, 2H) 5.13 (s, 2H) 6.96-7.01 (m, 2H) 7.21-7.30 (m, 3H) 7.72 (t, J = 7.5 Hz, 1H) 7.87 (dd, J = 8.0, 0.8 Hz, 1H) 8.22 (s, 1H) 8.54 (d, J = 7.8 Hz, 1H) | 1-{4-[2-fluoro-1-(fluoromethyl)ethoxy]phenyl}ethanamine |
| 22 | 2-(7-nitro-1H-benzimidazol-1-yl)-N-{1-[4-(1,1,2,2-tetrafluoroethoxy)phenyl]ethyl}acetamide | 441.2 | (400 MHz, DMSO-d6) δ ppm 1.38 (d, J = 6.8 Hz, 3H) 4.82-4.92 (m, 1H) 5.24 (s, 2H) 6.79 (tt, J = 52.0, 3.0 Hz, 1H) 7.19-7.25 (m, 2H) 7.36-7.44 (m, 3H) 7.98 (d, J = 8.0 Hz, 1H) 8.10 (dd, J = 8.0, 1.00 Hz, 1H) 8.40 (s, 1H) 8.75 (d, J = 7.8 Hz, 1H) | 1-[4-(1,1,2,2-tetrafluoroethoxy)phenyl]ethanamine |
| 23 | 2-(7-chloro-1H-benzimidazol-1-yl)-N-{1-[4-(1,1,2,2-tetrafluoroethoxy)phenyl]ethyl}acetamide | 430.2 | (400 MHz, DMSO-d6) δ ppm 1.40 (d, J = 7.0 Hz, 3H) 4.91-5.01 (m, 1H) 5.21 (s, 2H) 6.79 (tt, J = 51.9, 2.9 Hz, 1H) 7.17 (t, J = 7.8 Hz, 1H) 7.20-7.26 (m, 3H) 7.41-7.46 (m, 2H) 7.62 (dd, J = 7.8, 1.25 Hz, 1H) 8.20 (s, 1H) 8.79 (d, J = 7.8 Hz, 1H) | 1-[4-(1,1,2,2-tetrafluoroethoxy)phenyl]ethanamine |
| 24 | 2-(7-cyano-1H-benzimidazol-1-yl)-N-(1-{4-[2-fluoro-1-(fluoromethyl)ethoxy]phenyl}ethyl)acetamide | 399.2 | (400 MHz, DMSO-d6) δ ppm 1.38 (d, J = 7.0 Hz, 3H) 4.55-4.79 (m, 4H) 4.80-4.96 (m, 2H) 5.16-5.28 (m, 2H) 6.95-7.00 (m, 2H) 7.26-7.32 (m, 2H) 7.35 (t, J = 7.9 Hz, 1H) 7.71 (d, J = 7.5 Hz, 1H) 8.02 (dd, J = 8.0, 0.8 Hz, 1H) 8.35 (s, 1H) 8.75 (d, J = 7.8 Hz, 1H) | 1-{4-[2-fluoro-1-(fluoromethyl)ethoxy]phenyl}ethanamine |
| 25 | 2-(7-cyano-1H-benzimidazol-1-yl)-N-{1-[4-(2,2,2-trifluoroethoxy)phenyl]ethyl}acetamide | 403.0 | (400 MHz, CD3OD) δ ppm 1.49 (d, J = 7.07 Hz, 3H), 4.40 (q, J = 8.34 Hz, 2H), 5.00 (q, J = 6.95 Hz, 1H), 5.25 (s, 2H), 6.91 (d, J = 8.59 Hz, 2H), 7.31 (d, J = 8.59 Hz, 2H), 7.37 (t, J = 7.83 Hz, 1H), 7.64 (d, J = 7.33 Hz, 1H), 7.96 (d, J = 7.83 Hz, 1H), 8.16 (s, 1H) | 1-[4-(2,2,2-trifluoroethoxy)phenyl]ethanamine |
| 26 | N-(1-{5-chloro-6-[2-fluoro-1-(fluoromethyl)ethoxy] | 454.0 | (400 MHz, CD3OD) δ ppm 1.49 (d, J = 7.07 Hz, 3H), 4.66-4.69 (m, 2H), 4.77-4.81 (m, 2H), | 1-{5-chloro-6-[2-fluoro-1-(fluoro- |

TABLE 2-continued

| Ex. # | Name | MW found [M + H] | $^1$H NMR | Starting material |
|---|---|---|---|---|
| | pyridin-3-yl}ethyl)-2-(7-nitro-1H-benzimidazol-1-yl)acetamide | | 4.88-4.95 (m, 1H), 5.30 (s, 2H), 5.61 (tt, J = 19.96, 4.55 Hz, 1H), 7.40 (t, J = 8.08 Hz, 1H), 7.79 (d, J = 2.02 Hz, 1H), 8.0-8.05 (m, 3H), 8.29 (s, 1H) | methyl)ethoxy]pyridin-3-yl}ethanamine |
| 27 | 2-(7-cyano-1H-benzimidazol-1-yl)-N-{1-[4-[2-fluoro-1-(fluoromethyl)ethoxy]-2-(trifluoromethyl)phenyl]ethyl}acetamide | 467.0 | (400 MHz, CD$_3$OD) δ ppm 1.48 (d, J = 6.82 Hz, 3H), 4.56-4.94 (m, 5H), 5.28-5.35 (m, 1H), 5.33 (s, 2H), 7.24 (d, J = 2.53 Hz, 1H), 7.30 (dd, J = 8.59, 2.78 Hz, 1H), 7.37-7.41 (t, J = 7.83 Hz, 1H), 7.65-7.71 (m, 2H), 7.97 (dd, J = 8.08, 0.9 Hz, 1H), 8.25 (s, 1H) | 1-[4-[2-fluoro-1-(fluoromethyl)ethoxy]-2-(trifluoromethyl)phenyl]ethanamine |
| 28 | N-(1-{2-chloro-4-[2-fluoro-1-(fluoromethyl)ethoxy]phenyl}ethyl)-2-(7-cyano-1H-benzimidazol-1-yl)acetamide | 433.0 | (400 MHz, CD$_3$OD) δ ppm 1.46 (d, J = 7.07 Hz, 3H), 4.51-4.79 (m, 5H), 5.27-5.34 (m, 1H), 5.31 (s, 2H), 6.94 (dd, J = 8.59, 2.53 Hz, 1H), 7.00 (d, J = 2.78 Hz, 1H), 7.36 (t, J = 8.07 Hz, 1H), 7.42 (d, J = 8.59 Hz, 1H), 7.63 (br.d, J = 7.58 Hz, 1H), 7.95 (br.d, J = 8.08 Hz, 1H), 8.20 (s, 1H) | 1-{2-chloro-4-[2-fluoro-1-(fluoromethyl)ethoxy]phenyl}ethanamine |
| 29 | 2-(7-nitro-1H-benzimidazol-1-yl)-N-{1-[5-(trifluoromethyl)pyridin-2-yl]propyl}acetamide | 408.0 | (400 MHz, CD$_3$OD) δ ppm 0.99 (t, J = 7.33 Hz, 3H), 1.79-2.04 (m, 2H), 4.84-4.90 (m, 1H), 5.40 (dd, J = 17.18, 8.59 Hz, 2H), 7.40 (t, J = 8.08 Hz, 1H), 7.57 (br.d, J = 8.34 Hz, 1H), 7.99-8.08 (m, 3H), 8.30 (s, 1H), 8.80 (br.s, 1H) | 1-[5-(trifluoromethyl)pyridin-2-yl]propan-1-amine |
| 30 | 2-(7-nitro-1H-benzimidazol-1-yl)-N-{1-[5-(trifluoromethyl)pyridin-2-yl]ethyl}acetamide | 394 | (400 MHz, CD$_3$OD) δ ppm 1.53 (d, J = 7.07 Hz, 1H), 5.04 (q, J = 7.07 Hz, 1H), 5.38 (s, 2H), 7.39 (t, J = 8.08 Hz, 1H), 7.60 (d, J = 8.08 Hz, 1H), 8.00-8.08 (m, 3H), 8.30 (s, 1H), 8.79 (br.s, 1H) | 1-[5-(trifluoromethyl)pyridin-2-yl]ethanamine |
| 31 | 2-(7-chloro-1H-benzimidazol-1-yl)-N-{1-[3-chloro-5-(trifluoromethyl)pyridin-2-yl]ethyl}acetamide | 416.9 | (400 MHz, CD$_3$OD) δ ppm 1.51 (d, J = 6.82 Hz, 3H), 5.34 (dd, J = 17.4, 10.1 Hz, 2H), 5.61 (q, J = 6.82 Hz, 1H), 7.19-7.26 (m, 2H), 7.61 (dd, J = 7.07, 1.8 Hz, 1H), 8.15 (s, 1H), 8.20 (d, J = 2.02 Hz, 1H), 8.80 (br.s, 1H) | 1-[3-chloro-5-(trifluoromethyl)pyridin-2-yl]ethanamine |
| 32 | N-{1-[3-chloro-5-(trifluoromethyl)pyridin-2-yl]ethyl}-2-(7-nitro-1H-benzimidazol-1-yl)acetamide | 427.9 | (400 MHz, CD$_3$OD) δ ppm 1.49 (d, J = 6.82 Hz, 3H), 5.37 (dd, J = 17.2, 10.6 Hz, 2H), 5.51 (q, J = 6.82 Hz, 1H), 7.42 (t, J = 8.08 Hz, 1H), 8.01-8.06 (m, 2H), 8.18 (d, J = 2.02 Hz, 1H), 8.31 (s, 1H), 8.82 (br.s, 1H) | 1-[3-chloro-5-(trifluoromethyl)pyridin-2-yl]ethanamine |
| 33 | N-{1-[5-chloro-6-(2-fluoroethoxy)pyridin-3-yl]ethyl}-2-(7-nitro-1H-benzimidazol-1-yl)acetamide | 422.0 | (400 MHz, CD$_3$OD) δ ppm 1.48 (d, J = 7.07 Hz, 3H), 4.53-4.56 (m, 1H), 4.60-4.63 (m, 1H), 4.66-4.69 (m, 1H), 4.78-4.81 (m, 1H), 4.87-4.95 (m, 1H), 5.25 (s, 2H), 7.38 (t, J = 7.9 Hz, 1H), 7.71 (d, J = 2.02 Hz, 1H), 7.97 (d, J = 2.3 Hz, 1H), 8.00-8.04 (m, 2H), 8.20 (s, 1H) | 1-[5-chloro-6-(2-fluoroethoxy)pyridin-3-yl]ethanamine |
| 34 | 2-(7-chloro-1H-benzimidazol-1-yl)-N-{1-[4-(trifluoromethyl)phenyl]ethyl}acetamide | 382.0 | (400 MHz, CD$_3$OD) δ ppm 1.51 (d, J = 6.82 Hz, 3H), 5.10 (q, J = 6.82 Hz, 1H), 5.29 (dd, J = 17.2, 3.8 Hz, 2H), 7.18-7.26 (m, 2H), 7.53 (d, J = 8.08 Hz, 2H), 7.58-7.64 (m, 3H), 8.14 (s, 1H) | 1-[4-(trifluoromethyl)phenyl]ethanamine |
| 35 | 2-(7-chloro-1H-benzimidazol-1-yl)-N-[1-(6-isopropoxypyridin-3-yl)ethyl]acetamide | 373.1 | (400 MHz, CD$_3$OD) δ ppm 1.31 (d, J = 6.06 Hz, 6H), 1.50 (d, J = 6.82 Hz, 3H), 5.02 (q, J = 6.92 Hz, 1H), 5.15-5.23 (m, 1H), 5.27 (dd, J = 17.2, 5.3 Hz, 2H), 6.70 (d, J = 8.59 Hz, 1H), 7.20-7.27 (m, 2H), 7.61 (dd, J = 7.33, 1.8 Hz, 1H), 7.65 (d, J = 8.59, 2.5 Hz, 1H), 8.08 (d, J = 2.5 Hz, 1H), 8.15 (s, 1H) | 1-(6-isopropoxypyridin-3-yl)ethanamine |

TABLE 2-continued

| Ex. # | Name | MW found [M + H] | $^1$H NMR | Starting material |
|---|---|---|---|---|
| 36 | 2-(7-nitro-1H-benzimidazol-1-yl)-N-{1-[4-(trifluoromethoxy)phenyl]ethyl}acetamide | 408.9 | (400 MHz, CD$_3$OD) δ ppm 1.49 (d, J = 7.07 Hz, 3H), 4.97 (q, (J = 7.07 Hz, 1H), 5.34 (s, 2H), 7.22 (d, J = 8.08 Hz, 2H), 7.40-7.45 (m, 3H), 8.05 (d, J = 8.08, 2H), 8.30 (s, 1H) | 1-[4-(trifluoromethoxy)phenyl]ethanamine |
| 37 | 2-(7-nitro-1H-benzimidazol-1-yl)-N-{1-[4-(trifluoromethyl)phenyl]ethyl}acetamide | 392.9 | (400 MHz, CD$_3$OD) δ ppm 1.51 (d, J = 6.82 Hz, 3H), 5.01 (q, J = 6.82 Hz, 1H), 5.36 (s, 2H), 7.42 (t, J = 8.08 Hz, 1H), 7.52 (d, J = 8.34 Hz, 2H), 7.62 (d, J = 8.34 Hz, 2H), 8.05 (d, J = 8.08 Hz, 2H), 8.30 (s, 1H) | 1-[4-(trifluoromethyl)phenyl]ethanamine |
| 38 | N-[1-(6-isopropoxypyridin-3-yl)ethyl]-2-(7-nitro-1H-benzimidazol-1-yl)acetamide | 384.0 | (400 MHz, CD$_3$OD) δ ppm 1.31 (d, J = 6.06 Hz, 6H), 1.49 (d, J = 7.07 Hz, 3H), 4.93 (q, J = 7.07 Hz, 1H), 5.14-5.22 (m, 1H), 5.30 (s, 2H), 6.70 (d, J = 8.59 Hz, 1H), 7.43 (t, J = 8.08 Hz, 1H), 7.65 (dd, J = 8.59, 2.5 Hz, 1H), 8.03-8.07 (m, 3H), 8.30 (s, 1H) | 1-(6-isopropoxypyridin-3-yl)ethanamine |
| 39 | N-{1-[4-(cyclopentyloxy)-3-fluoro-phenyl]ethyl}-2-(7-nitro-1H-benzimidazol-1-yl)acetamide | 426.9 | (400 MHz, CD$_3$OD) δ ppm 1.45 (d, J = 6.82 Hz, 3H), 1.59-1.70 (m, 2H), 1.75-1.95 (m, 6H), 4.80-4.85 (m, 1H), 4.89 (q, J = 6.82 Hz, 1H), 5.31 (s, 2H), 6.96-7.10 (m, 3H), 7.43 (t, J = 8.08 Hz, 1H), 8.05 (d, J = 8.08 Hz, 2H), 8.30 (s, 1H) | 1-[4-(cyclopentyloxy)-3-fluoro-phenyl]ethanamine |
| 40 | N-[1-(4-cyclopropylphenyl)ethyl]-2-(7-nitro-1H-benzimidazol-1-yl)acetamide | 365.0 | (400 MHz, CHLOROFORM-d) δ ppm 0.60-0.70 (m, 2H) 0.88-0.98 (m, 2H) 1.48 (d, J = 7.07 Hz, 3H) 1.77-1.91 (m, 1H) 4.93-5.09 (t, J = 6.57 Hz, 1H) 5.21 (s, 2H) 6.34 (s, 1H) 7.01 (d, J = 6.06 Hz, 2H) 7.18 (d, J = 8.08 Hz, 2H) 7.43 (t, J = 8.21 Hz, 1H) 8.10 (d, J = 8.08 Hz, 1H) 8.14 (d, J = 8.08 Hz, 1H) 8.49 (s, 1H) | 1-(4-cyclopropyl-phenyl)ethanamine |
| 41 | N-[1-(4-ethynyl-phenyl)ethyl]-2-(7-nitro-1H-benzimidazol-1-yl)acetamide | 349.1 | (400 MHz, CD$_3$OD) δ ppm 1.37 (d, J = 7.07 Hz, 3H) 3.35 (s, 1H) 4.85 (q, J = 14.15, 7.07 Hz, 1H) 5.23 (s, 2H) 7.21 (d, J = 8.34 Hz, 2H) 7.32 (d, J = 8.34 Hz, 2H) 7.95 (d, J = 7.83 Hz, 2H) 8.26 (s, 1H) 8.68 (d, J = 7.58 Hz, 1H) | 1-(4-ethynyl-phenyl)ethanamine |
| 42 | 2-(7-chloro-1H-benzimidazol-1-yl)-N-[1-(4-ethynyl-phenyl)ethyl]acetamide | 338.0 | 1H NMR (400 MHz, CD$_3$OD) δ ppm 1.39 (d, J = 7.07 Hz, 3H) 3.36 (s, 1H) 4.93 (q, J = 14.15, 7.07 Hz, 1H) 5.20 (d, J = 4.55 Hz, 2H) 7.10-7.19 (m, 2H) 7.23 (d, J = 8.34 Hz, 2H) 7.32 (d, J = 8.08 Hz, 2H) 7.52 (dd, J = 7.71, 1.39 Hz, 1H) 8.05 (s, 1H) | 1-(4-ethynyl-phenyl)ethanamine |
| 43 | N-{1-[5-(cyclopropylmethoxy)pyridin-2-yl]ethyl}-2-(7-nitro-1H-benzimidazol-1-yl)acetamide | 396.0 | (400 MHz, CD$_3$OD) δ ppm 0.22-0.32 (m, 2H) 0.46-0.57 (m, 2H) 1.08-1.23 (m, 1H) 1.37 (d, J = 6.82 Hz, 3H) 3.78 (d, J = 7.07 Hz, 2H) 4.84 (q, J = 6.99 Hz, 1H) 5.25 (s, 2H) 7.23 (d, J = 2.02 Hz, 2H) 7.32 (t, J = 8.08 Hz, 1H) 7.95 (dd, J = 8.21, 1.39 Hz, 2H) 8.03 (t, J = 1.77 Hz, 1H) 8.21 (s, 1H) | 1-[5-(cyclopropylmethoxy)pyridin-2-yl]ethanamine |
| 44 | N-[1-(5-isopropoxypyridin-2-yl)ethyl]-2-(7-nitro-1H-benzimidazol-1-yl)acetamide | 384.1 | (400 MHz, CD$_3$OD) δ ppm 1.22 (d, J = 5.81 Hz, 6H) 1.37 (d, J = 7.07 Hz, 3H) 4.45-4.61 (m, 1H) 4.84 (q, J = 13.89, 6.82 Hz, 1H) 5.25 (s, 2H) 7.23 (d, J = 1.77 Hz, 2H) 7.31 (t, J = 8.08 Hz, 1H) 7.94 (dd, J = 8.08, 2.02 Hz, 2H) 8.00 (t, J = 1.64 Hz, 1H) 8.21 (s, 1H); | 1-(5-isopropoxypyridin-2-yl)ethanamine |

TABLE 2-continued

| Ex. # | Name | MW found [M + H] | ¹H NMR | Starting material |
|---|---|---|---|---|
| 45 | 2-(7-acetyl-1H-benzimidazol-1-yl)-N-[(1S)-1-(4-tert-butylphenyl)ethyl]acetamide | 378.3 | ¹H NMR (400 MHz, METHANOL-D4) δ ppm 1.29 (s, 9H) 1.44 (d, J = 7.03 Hz, 3H) 2.41 (s, 3H) 4.88 (q, J = 7.03 Hz, 1H) 5.25 (s, 2H) 7.24 (d, J = 8.20 Hz, 2H) 7.29-7.42 (m, 3H) 7.75 (d, J = 6.64 Hz, 1H) 7.87 (d, J = 8.98 Hz, 1H) 8.14 (s, 1H) | (1S)-1-(4-tert-butylphenyl)ethanamine |
| 46 | N-{1-[4-[(1-Methylpiperidin-4-yl)oxy]-3-(trifluoromethyl)phenyl]ethyl}-2-(7-nitro-1H-benzimidazol-1-yl)acetamide | 506.0 | (400 MHz, DMSO-D6) δ ppm 1.36 (d, J = 7.0 Hz, 3H), 1.63-1.71 (m, 2H), 1.85-1.93 (m, 2H), 2.16 (s, 3H), 2.22-2.27 (m, 2H), 2.46-2.48 (m, 2H), 4.56-4.62 (m, 1H), 4.81-4.87 (m, 1H), 5.21 (s, 2H), 7.22 (d, J = 8.5 Hz, 1H), 7.39 (t, J = 8.0 Hz, 1H), 7.48-7.51 (m, 1H), 7.53-7.54 (m, 1H), 7.96 (d, J = 8.0 Hz, 1H), 8.09 (d, J = 8.0 Hz, 1H), 8.39 (s, 1H), 8.74 (d, J = 7.8 Hz, 1H). | 1-[4-[(1-methylpiperidin-4-yl)oxy]-3-(trifluoromethyl)phenyl]ethanamine |
| 47 | N-{1-[4-{[(2S)-2-Methoxypropyl]oxy}-3-(trifluoromethyl)phenyl]ethyl}-2-(7-nitro-1H-benzimidazol-1-yl)acetamide | 481.0 | (400 MHz, DMSO-D6) δ ppm 1.18 (d, J = 6.5 Hz, 3H), 1.37 (d, J = 7.0 Hz, 3H), 3.32 (s, 3H), 3.63-3.69 (m, 1H), 3.99-4.10 (m, 2H), 4.83-4.90 (m, 1H), 5.22 (s, 2H), 7.20 (d, J = 8.5 Hz, 1H), 7.39 (t, J = 8.0 Hz, 1H), 7.51-7.55 (m, 2H), 7.97 (d, J = 8.0 Hz, 1H), 8.09 (d, J = 8.0 Hz, 1H), 8.40 (s, 1H), 8.73 (d, J = 7.8 Hz, 1H). | {1-[4-{[(2S)-2-methoxypropyl]oxy}-3-(trifluoromethyl)phenyl]ethyl}amine |
| 48 | N-{1-methyl-2-[3-(trifluoromethyl)phenoxy]ethyl}-2-(7-nitro-1H-benzimidazol-1-yl)acetamide | 423.0 | (400 MHz, DMSO-d6) δ ppm 8.39-8.47 (m, 2H) 8.11 (dd, J = 8.08, 1.01 Hz, 1H) 7.98 (dd, J = 7.96, 0.88 Hz, 1H) 7.53 (t, J = 7.83 Hz, 1H) 7.40 (t, J = 8.08 Hz, 1H) 7.23-7.33 (m, 3H) 5.19 (s, 2H) 3.89-4.12 (m, 3H) 1.19 (d, J = 6.57 Hz, 3H) | 1-[3-(trifluoromethyl)phenoxy]propan-2-amine |
| 49 | N-[2-(4-chlorophenyl)-1-methylethyl]-2-(7-nitro-1H-benzimidazol-1-yl)acetamide | 373.0 | (400 MHz, DMSO-d6) δ ppm 8.39 (s, 1H) 8.23 (d, J = 7.83 Hz, 1H) 8.10 (d, J = 8.08 Hz, 1H) 7.98 (d, J = 7.33 Hz, 1H) 7.37-7.43 (m, 1H) 7.29-7.35 (m, 2H) 7.21 (d, J = 8.34 Hz, 2H) 5.06-5.18 (m, 2H) 3.80-3.93 (m, 1H) 2.58-2.77 (m, 2H) 1.03 (d, J = 6.57 Hz, 3H) | 1-(4-chlorophenyl)propan-2-amine |
| 50 | N-[(3R)-5-Methoxy-3,4-dihydro-2H-chromen-3-yl]-2-(7-nitro-1H-benzimidazol-1-yl)acetamide | 383.0 | (400 MHz, DMSO-D6) δ ppm 2.50-2.55 (m, 1H), 2.81-2.87 (m, 1H), 3.78 (s, 3H), 3.80-3.84 (m, 1H), 4.00-4.10 (m, 2H), 5.15-5.24 (m, 2H), 6.45 (d, J = 8.3 Hz, 1H), 6.55 (d, J = 8.0 Hz, 1H), 7.08 (t, J = 8.3 Hz, 1H), 7.41 (t, J = 8.0 Hz, 1H), 7.99 (d, J = 7.8 Hz, 1H), 8.11 (d, J = 8.0 Hz, 1H), 8.41 (s, 1H), 8.49 (d, J = 7.0 Hz, 1H). | (3R)-5-methoxychroman-3-amine |
| 51 | N-[(3R)-8-Fluoro-5-methoxy-3,4-dihydro-2H-chromen-3-yl]-2-(7-nitro-1H-benzimidazol-1-yl)acetamide | 401.0 | (400 MHz, DMSO-D6) δ ppm 2.53-2.59 (m, 1H), 2.83-2.89 (m, 1H), 3.76 (s, 3H), 3.93-3.97 (m, 1H), 4.07-4.16 (m, 2H), 5.19 (s, 2H), 6.48 (dd, J = 9.0, 3.5 Hz, 1H), 7.02 (dd, J = 10.8, 9.0 Hz, 1H), 7.41 (t, J = 8.0 Hz, 1H), 8.0 (d, J = 8.0 Hz, 1H), 8.11 (dd, J = 7.9, 0.9 Hz, 1H), 8.41 (s, 1H), 8.55 (d, J = 7.0 Hz, 1H). | (3R)-8-fluoro-5-methoxy-chroman-3-amine |
| 52 | N-[(1S)-1-(4-tert-butylphenyl)ethyl]-2-(6,7-difluoro-1H- | 372.3 | (400 MHz, DMSO-D6) δ ppm 1.16-1.26 (m, 9H), 1.35 (d, J = 7.03 Hz, 3H), 4.81-4.90 (m, | [(1S)-1-(4-tert-butylphenyl)ethyl]amine |

TABLE 2-continued

| Ex. # | Name | MW found [M + H] | ¹H NMR | Starting material |
|---|---|---|---|---|
| | benzimidazol-1-yl)acetamide | | 1H), 5.12-5.25 (m, 2H), 7.21-7.26 (m, 2H), 7.26-7.34 (m, 3H), 7.69 (d, J = 7.42 Hz, 1H), 7.98 (d, J = 7.81 Hz, 1H), 8.33 (s, 1H), 8.75 (d, J = 7.81 Hz, 1H) | |
| 53 | N-[1-(4-tert-butyl-phenyl)ethyl]-2-(6,7-difluoro-1H-benzimidazol-1-yl)acetamide | 372.0 | (400 MHz, DMSO-D6) δ ppm 1.26 (s, 9H), 1.37 (d, J = 6.84 Hz, 3H), 4.85-4.94 (m, 1H), 5.05 (s, 2H), 7.17-7.26 (m, 3H), 7.31-7.36 (m, 2H), 7.43-7.48 (m, 1H), 8.19 (s, 1H), 8.76 (d, J = 7.81 Hz, 1H) | [1-(4-tert-butyl-phenyl)ethyl]amine |
| 54 | N-[1-(4-tert-butyl-phenyl)ethyl]-2-(7-cyano-1H-benzimidazol-1-yl)acetamide | 361.3 | ¹H NMR (400 MHz, METHANOL-D4) δ ppm 1.28 (s, 9H) 1.48 (d, J = 7.03 Hz, 3H) 4.99 (q, J = 7.03 Hz, 1H) 5.30 (s, 2H) 7.27 (d, 2H) 7.34 (d, 2H) 7.39 (dd, J = 8.20, 7.62 Hz, 1H) 7.68 (dd, J = 7.62, 0.59 Hz, 1H) 7.97 (dd, J = 8.20, 0.98 Hz, 1H) 8.25 (s, 1H). | 1-(4-tert-butylphenyl) ethanamine |
| 55 | 2-(7-cyano-1H-benzimidazol-1-yl)-N-[1-(4-isopropyl-phenyl)ethyl]acetamide | 347.0 | (400 MHz, CD3OD) δ ppm 1.19-1.22 (m, 6H), 1.48 (d, J = 7.0 Hz, 3H), 2.77-2.91 (m, 1H), 5.38 (s, 2H), 7.12-7.20 (m, 2H), 7.23-7.31 (m, 2H), 7.45-7.54 (m, 1H), 7.75-7.83 (m, 1H), 8.03 (dd, J = 1.0, 8.2 Hz, 1H), 8.64 (s, 1H), 8.87 (br d, J = 7.4 Hz, 1H) | [1-(4-isopropyl-phenyl)ethyl]amine |
| 56 | 2-(7-cyano-1H-benzimidazol-1-yl)-N-{1-[4-(trifluoro-methyl)phenyl]ethyl} acetamide | 372.8 | (400 MHz, CD3OD) δ ppm 1.52 (d, J = 7.0 Hz, 3H), 5.08 (q, J = 7.0 Hz, 1H), 5.35 (s, 2H), 7.34-7.42 (m, 1H), 7.51-7.63 (m, 4H), 7.63-7.70 (m, 1H), 7.97 (dd, J = 0.8, 8.2 Hz, 1H), 8.27 (s, 1H) | {1-[4-(trifluoro methyl)phenyl] ethyl}amine |
| 57 | 2-(7-fluoro-1H-benzimidazol-1-yl)-N-[1-(4-isopropyl-phenyl)ethyl]acetamide | 340.0 | (400 MHz, CD3OD) δ ppm 1.21 (d, J = 6.2 Hz, 6H), 1.48 (d, J = 6.8 Hz, 3H), 2.80-2.92 (m, 1H), 4.94-5.06 (m, 1H), 5.20-5.35 (m, 2H), 7.14-7.21 (m, 2H), 7.21-7.33 (m, 3H), 7.41-7.53 (m, 1H), 7.60 (d, J = 8.0 Hz, 1H), 8.88-8.96 (m, 1H), 9.01 (br s, 1H) | [1-(4-isopropylphenyl) ethyl]amine |
| 58 | 2-(7-cyano-1H-benzimidazol-1-yl)-N-{(1S)-1-[4-(trifluoromethyl) phenyl]ethyl} acetamide | 372.8 | (400 MHz, CD3OD) δ ppm 1.52 (d, J = 7.0 Hz, 3H), 4.98-5.15 (m, 1H), 5.35 (s, 2H), 7.32-7.45 (m, 1H), 7.51-7.63 (m, 4H), 7.68 (dd, J = 0.9, 8.2 Hz, 1H), 7.97 (dd, J = 1.0, 8.2 Hz, 1H), 8.26 (s, 1H) | {(1S)-1-[4-(trifluoro-methyl)phenyl] ethyl}amine |
| 59 | 2-(6,7-difluoro-1H-benzimidazol-1-yl)-N-{1-[4-(trifluoro-methyl)phenyl]ethyl} acetamide | 383.8 | (400 MHz, CD3OD) δ ppm 1.52 (d, J = 7.0 Hz, 3H), 5.05-5.12 (m, 1H), 5.18-5.27 (m, 2H), 7.24-7.36 (m, 1H), 7.46-7.56 (m, 3H), 7.58-7.66 (m, 2H), 8.59 (br s, 1H), 9.02 (br d, J = 7.4 Hz, 1H) | {1-[4-(trifluoro-methyl)phenyl] ethyl}amine |
| 61 | 2-(7-cyano-1H-benzimidazol-1-yl)-N-{1-[4-(trifluoro-methoxy)phenyl]ethyl} acetamide | 388.8 | (400 MHz, CD3OD) δ ppm 1.51 (d, J = 7.0 Hz, 3H), 4.96-5.12 (m, 1H), 5.40 (s, 2H), 7.15-7.26 (m, 2H), 7.39-7.55 (m, 3H), 7.78 (dd, J = 0.8, 7.6 z, 1H), 8.02 (dd, J = 1.0, 8.4 Hz, 1H), 8.60 (s, 1H), 8.90-8.99 (m, 1H) | {1-[4-(trifluoromethoxy) phenyl]ethyl} amine |
| 62 | methyl (4-tert-butylphenyl) {[(6,7-difluoro-1H-benzimidazol-1-yl)acetyl]amino}acetate | 415.8 | (400 MHz, DMSO-D6) δ ppm 1.25 (s, 9H), 3.59 (s, 3H), 5.05-5.17 (m, 2H), 5.36 (d, J = 6.84 Hz, 1H), 7.15-7.25 (m, 1H), 7.27-7.33 (m, 2H), 7.39-7.46 (m, 3H), 8.18 (s, 1H), 9.23 (d, J = 7.03 Hz, 1H) | methyl amino(4-tert-butyl-phenyl)acetate |
| 63 | 2-(7-fluoro-1H-benzimidazol-1-yl)-N-{1-[4-(trifluoro-methyl)phenyl]ethyl} | 365.8 | (400 MHz, CD3OD) δ ppm 1.50 (d, J = 7.0 Hz, 3H), 5.05-5.19 (m, 3H), 7.00 (dd, J = 8.1, 11.4 Hz, 1H), 7.14-7.23 (m, 1H), | {1-[4-(trifluoro-methyl)phenyl] ethyl}amine |

TABLE 2-continued

| Ex. # | Name | MW found [M + H] | ¹H NMR | Starting material |
|---|---|---|---|---|
|  | acetamide |  | 7.46 (d, J = 8.2 Hz, 1H), 7.48-7.54 (m, 2H), 7.55-7.63 (m, 2H), 8.11 (s, 1H) |  |
| 64 | N-[1-(5-tert-butylpyridin-2-yl)ethyl]-2-(7-cyano-1H-benzimidazol-1-yl)acetamide | 362.0 | (400 MHz, CHLOROFORM-D.) δ ppm 1.34 (s, 9H), 1.50 (d, J = 6.84 Hz, 3H), 5.08-5.16 (m, 1H), 5.12-5.26 (m, 2H), 7.15 (d, J = 7.81 Hz, 1H), 7.35 (dd, J = 8.11, 7.71 Hz, 1H), 7.45 (d, J = 6.44 Hz, 1H), 7.61 (dd, J = 7.62, 0.98 Hz, 1H), 7.66 (dd, J = 8.20, 2.54 Hz, 1H), 8.05 (s, 1H), 8.07 (dd, J = 8.20, 0.98 Hz, 1H), 8.49 (dd, J = 2.54, 0.59 Hz, 1H) | [1-(5-tert-butylpyridin-2-yl)ethyl]amine |
| 68 | 2-(7-cyano-1H-benzimidazol-1-yl)-N-{1-[3-fluoro-4-(trifluoromethyl)phenyl]ethyl}acetamide | 390.8 | (400 MHz, CD3OD) δ ppm 1.52 (d, J = 7.0 Hz, 3H), 5.01-5.12 (m, 1H), 5.35-5.49 (m, 2H), 7.30-7.38 (m, 2H), 7.45-7.53 (m, 1H), 7.61 (t, J = 7.7 Hz, 1H), 7.78 (dd, J = 1.0, 7.6 Hz, 1H), 8.03 (dd J = 1, 8.2 Hz, 1H), 8.61 (s, 1H), 9.03-9.12 (m, 1H) | {1-[3-fluoro-4-(trifluoromethyl)phenyl]ethyl}amine |
| 69 | N-[1-(5-tert-butyl-2-thienyl)ethyl]-2-(6,7-difluoro-1H-benzimidazol-1-yl)acetamide | 377.8 | (400 MHz, DMSO-D6) δ ppm 1.27 (s, 9H), 1.42 (d, J = 7.03 Hz, 3H), 4.97-5.07 (m, 2H), 5.04-5.14 (m, 1H), 6.66 (d, J = 3.52 Hz, 1H), 6.72 (dd, J = 3.61, 1.07 Hz, 1H), 7.17-7.26 (m, 1H), 7.42-7.46 (m, 1H), 8.21 (s, 1H), 8.81 (d, J = 8.40 Hz, 1H). | [1-(5-tert-butyl-2-thienyl)ethyl]amine |
| 70 | N-[1-(5-tert-butyl-2-thienyl)ethyl]-2-(7-fluoro-1H-benzimidazol-1-yl)acetamide | 360.0 | (400 MHz, DMSO-D6) δ ppm 1.27 (s, 9H), 1.42 (d, J = 6.84 Hz, 3H), 4.99-5.13 (m, 3H), 6.67 (d, J = 3.52 Hz, 1H), 6.72 (dd, J = 3.61, 1.07 Hz, 1H), 7.02-7.11 (m, 1H), 7.14-7.25 (m, 1H), 7.49 (d, J = 8.01 Hz, 1H), 8.38 (s, 1H), 8.81 (d, J = 8.20 Hz, 1H). | [1-(5-tert-butyl-2-thienyl)ethyl]amine |
| 71 | N-[1-(5-tert-butyl-2-thienyl)ethyl]-2-(7-cyano-1H-benzimidazol-1-yl)acetamide | 367.0 | (400 MHz, METHANOL-D4) δ ppm 1.32 (s, 9H), 1.56 (d, J = 6.84 Hz, 3H), 5.18-5.27 (m, 1H), 5.26-5.37 (m, 2H), 6.65 (d, J = 3.52 Hz, 1H), 6.79 (d, J = 3.52 Hz, 1H), 7.44 (t, J = 7.03 Hz, 1H), 7.72 (d, J = 7.42 Hz, 1H), 8.03 (s, 1H), 8.49 (s, 1H), 8.86 (d, J = 7.62 Hz, 1H). | [1-(5-tert-butyl-2-thienyl)ethyl]amine |

Example 72

N-[1-(6-tert-butyl-2-methoxypyridin-3-yl)ethyl]-2-(7-cyano-1H-benzimidazol-1-yl)acetamide The title compound was synthesized according to the procedure described for the synthesis of 2-methylnicotinamide, starting from [1-(6-tert-butyl-2-methoxypyridin-3-yl)ethyl]amine (intermediate 27) (85 mg, 0.48 mmol), 7-cyanobenzimidazole-1-acetic acid (96 mg 0.48 mmol) HATU (173 mg, 0.5 mmol) and DIPEA (209 μl, 1.20 mmol). The product was recovered by filtration following precipitation induced by the addition of water. (Yield 27 mg, 46%). ¹H NMR (400 MHz, DMSO-D6) δ ppm 1.27 (s, 9 H), 1.32 (d, J=6.84 Hz, 3 H), 3.86 (s, 3 H), 5.02 (t, J=7.03 Hz, 1 H), 5.25 (d, J=4.69 Hz, 2 H), 6.91 (d, J=7.62 Hz, 1 H), 7.31-7.37 (m, 1 H), 7.62 (dd, J=7.62, 0.39 Hz, 1 H), 7.71 (dd, J=7.71, 1.07 Hz, 1 H), 8.01 (dd, J=8.20, 0.98 Hz, 1 H), 8.34 (s, 1 H), 8.78-8.83 (m, J=7.81 Hz, 1 H). MS [MH+] calc. 392.2086 found 392.3.

Example 73

N-[1-(6-tert-butyl-2-methylpyridin-3-yl)ethyl]-2-(6,7-difluoro-1H-benzimidazol-1-yl)acetamide The title compound was synthesized according to the procedure described for the synthesis of 2-methylnicotinamide, starting from [1-(6-tert-butyl-2-methylpyridin-3-yl)ethyl] amine (intermediate 32) (31.5 mg, 0.16 mmol), 6,7-difluorobenzimidazole-1-acetic acid (35 mg 0.16 mmol) HATU (38 mg, 0.18 mmol) and DIPEA (71 μl, 0.41 mmol). Water was added and the reaction concentrated. The mixture was partitioned between ethyl acetate and water, and extracted 3 more times with ethyl acetate. The product was then purified by silica gel flash chromatography with acetone/hexanes (Yield 25 mg, 40%). ¹H NMR (400 MHz, CD3OD-D4) d ppm 1.32 (s, 9 H), 1.47 (d, J=7.03 Hz, 3 H), 2.53-2.57 (m, 3 H), 5.04-5.15 (m, 2 H), 5.15-5.22 (m, 1 H), 7.16 (ddd, J=11.43, 8.79, 7.52 Hz, 1 H), 7.28 (d, J=8.20 Hz, 1 H), 7.41 (dd, J=8.89, 3.61 Hz, 1 H), 7.68 (d, J=8.20 Hz, 1 H), 8.11 (s, 1 H) MS [MH+] calc. 387.1996 found 387.3.

Example 74

N-[1-(6-tert-butyl-4-methylpyridin-3-yl)ethyl]-2-(7-cyano-1H-benzimidazol-1-yl)acetamide The title compound was synthesized according to the procedure described for the synthesis of 2-methylnicotinamide, starting from [1-(6-tert-butyl-4-methylpyridin-3-yl)ethyl] amine (intermediate 28) (52 mg, 0.27 mmol), 7-cyanobenzimidazole-1-acetic acid (54.4 mg, 0.27 mmol), HATU (108 mg, 0.28 mmol) and DIPEA (117 µL, 2.5 mmol). Water is added and the reaction is concentrated then purified by reverse phase chromatography. (Yield 31.3 mg, 31%). $^1$H NMR (400 MHz, DMSO-D6) δ ppm 1.27 (s, 9 H), 1.42 (d, J=7.03 Hz, 3 H), 2.29 (s, 3 H), 5.03-5.12 (m, 1 H), 5.13-5.27 (m, 2 H), 7.17 (s, 1 H), 7.34 (dd, J=8.11, 7.71 Hz, 1 H), 7.71 (dd, J=7.62, 0.78 Hz, 1 H), 8.01 (dd, J=8.01, 0.98 Hz, 1 H), 8.34 (s, 1 H), 8.47 (s, 1 H), 8.88 (d, J=7.81 Hz, 1 H). MS [MH+] calc. 376.2137 found 376.3.

Example 75

N-[1-(6-tert-butyl-2-chloropyridin-3-yl)ethyl]-2-(7-cyano-1H-benzimidazol-1-yl)acetamide The title compound was synthesized according to the procedure described for the synthesis of 2-methylnicotinamide, starting from [1-(6-tert-butyl-2-chloropyridin-3-yl)ethyl] amine (intermediate 26) (100 mg, 0.47 mmol), 7-cyanobenzimidazole-1-acetic acid (0.42 mmol), HATU (191 mg, 0.5 mmol) and DIPEA (182 µL, 1.41 mmol). The product was recovered by filtration following precipitation induced by the addition of water. Yield 111 mg, 67%.

$^1$H NMR (400 MHz, DMSO-D6) δ ppm 1.27 (s, 9 H), 1.38 (d, J=7.03 Hz, 3 H), 5.05-5.13 (m, 1 H), 5.21-5.32 (m, 2 H), 7.34 (dd, J=8.01, 7.62 Hz, 1 H), 7.43 (d, J=8.01 Hz, 1 H), 7.71 (dd, J=7.62, 0.98 Hz, 1 H), 7.86 (d, J=8.01 Hz, 1 H), 8.01 (dd, J=8.01, 0.98 Hz, 1 H), 8.34 (s, 1 H), 9.06 (d, J=7.23 Hz, 1 H). MS [MH+] calc. 396.1591 found 396.3.

Example 76

N-[1-(6-tert-butylpyridin-3-yl)ethyl]-2-(7-cyano-1H-benzimidazol-1-yl)acetamide

The title compound was synthesized according to the procedure described for the synthesis of 2-methylnicotinamide, starting from [1-(6-tert-butylpyridin-3-yl)ethyl]amine (intermediate 25) (93 mg, 0.52 mmol), 7-cyanobenzimidazole-1-acetic acid (100 mg, 0.5 mmol), HATU (198 mg, 0.52 mmol) and DIPEA (226 µL, 1.3 mmol). Water is added and the reaction is concentrated then purified by reverse phase chromatography. $^1$H NMR (400 MHz, DMSO-D6) δ ppm 1.26 (s, 9 H), 1.39 (d, J=7.03 Hz, 3 H), 4.87-4.97 (m, 1 H), 5.12-5.27 (m, 2 H), 7.32 (dd, J=8.01, 7.62 Hz, 1 H), 7.35 (d, J=8.20 Hz, 1 H), 7.66 (dd, J=8.30, 2.25 Hz, 1 H), 7.69 (dd, J=7.52, 0.88 Hz, 1 H), 7.99 (dd, J=8.20, 0.98 Hz, 1 H), 8.32 (s, 1 H), 8.45 (d, J=2.54 Hz, 1 H), 8.85 (d, J=7.42 Hz, 1 H). MS [MH+] calc. 362.1981 found 362.3.

Pharmacology 1. hVR1 FLIPR (Fluorometric Image Plate Reader) Screening Assay

Transfected CHO cells, stably expressing hVR1 (15,000 cells/well) are seeded in 50 ul media in a black clear bottom 384 plate (Greiner) and grown in a humidified incubator (37° C., 2% $CO_2$), 24-30 hours prior to experiment.

Subsequently, the media is removed from the cell plate by inversion and 2 µM Fluo-4 is added using a multidrop (Lab-systems). Following the 40 minutes dye incubation in the dark at 37° C. and 2% $CO_2$, the extracellular dye present is washed away using an EMBLA (Scatron), leaving the cells in 40 ul of assay buffer (1×HBSS, 10 mM D-Glucose, 1 mM $CaCl_2$, 10 mM HEPES, 10×7.5% $NaHCO_3$ and 2.5 mM Probenecid).

FLIPR Assay—$IC_{50}$ Determination Protocol

For $IC_{50}$ determinations the fluorescence is read using FLIPR filter 1 (em 520-545 nM). A cellular baseline recording is taken for 30 seconds, followed by a 20 µl addition of 10, titrated half-log concentrations of the test compound, yielding cellular concentration ranging from 3 µM to 0.1 nM. Data is collected every 2 seconds for a further 5 minutes prior to the addition of a VR1 agonist solution: 20-50 nM solution of capsaicin by the FLIPR pipettor. The FLIPR continues to collect data for a further 4 minutes. Compounds having antagonistic properties against the hVR1 will inhibit the increase in intracellular calcium in response to the capsaicin addition. This consequently leading to a reduction in fluorescence signal and providing a reduced fluorescence reading, compared with no compound, buffer controls. Data is exported by the FLIPR program as a sum of fluorescence calculated under the curve upon the addition of capsaicin. Maximum inhibition, Hill slope and $IC_{50}$ data for each compound are generated.

2. hVR1 FLIPR (Fluorometric Image Plate Reader) Screening Assay with HEK T-REX hVR1.

HEK T-REX hVR1 inducible cells are grown in supplemented DMEM medium (10% FBS, 2 mM Glutamine, 5 µg/ml Blasticidine & 350 µg/ml Zeocin). HEK cells are plated in 384-black polylysine coated plate (Costar) at 10000 cells/well/50 µl for 24 hours or 5,500 cells/well 48 hours in a humidified incubator (5% $CO_2$ and 37° C.) in DMEM medium without selection agent. HEK T-Rex hVR1 cells are induced with 0.1 µg/ml Tetracycline 16 hours prior the experiment.

Subsequently, the media is removed from the cell plate by inversion and 2 µM Fluo-4 is added using a multidrop (Lab-systems). Following the 30 to 40 minutes dye incubation in the dark at 37° C. and 2% $CO_2$, the extracellular dye present is washed away using an Microplate Washer Skatron Embla 384, leaving the cells in 25 µl of assay buffer (1×HBSS without $Ca^{++}$/$Mg^{++}$/sodium bicarbonate, 1 mM $CaCl_2$ & 5 mM D-Glucose).

FLIPR Assay—$IC_{50}$ Determination Protocol

For $IC_{50}$ determinations the fluorescence is read using FLIPR filter 1 (em 520-545 nM). A cellular baseline recording is taken for 10 seconds, followed by 12.5 µl addition of test compounds, 10 points dilution 3 fold concentration, yielding cellular concentration ranging from 22.5 µM to 0.1 nM. Data are collected every 2 seconds for a further 5 minutes prior to the addition of a VR1 agonist solution: 20 nM (or 50 nM) capsaicin solution is added by the FLIPR pipettor. The FLIPR continues to collect data for a further 4 minutes. Compounds having antagonistic properties against the hVR1 will inhibit the increase in intracellular calcium in response to the capsaicin addition. This consequently leading to a reduction in fluorescence signal and providing a reduced fluorescence reading, compared with no compound, buffer controls. Data is exported by the FLIPR program as a sum of fluorescence calculated under the curve upon the addition of capsaicin. Maximum inhibition, Hill slope and $IC_{50}$ data for each compound are generated.

3. DRGs were dissected out from adult Sprague Dawley rats (100-300 gr), and placed on ice in L15 Leibovitz medium. The ganglia were enzyme treated with Collagenase 80 U/ml+ Dispase 34 U/ml dissolved in DMEM+5% serum, overnight at 37° C. The next day, cells were triturated with fire polished pasteur pipettes, and seeded in the center of 58 mm diameter Nunc cell dishes coated with Poly-D Lysine (1 mg/ml). The DRGs were cultured in a defined medium without foetal bovine serum, containing Dulbecco's MEM/NUT MIX F-12 (1:1) without L-glutamine but with pyridoxine, 6 mg/mL D(+)-Glucose, 100 μg/mL apo-transferrin, 1 mg/mL BSA, 20 μg/mL insulin, 2 mM L-glutamine, 50 IU/mL Penicillin, 50 μg/mL Streptomycin and 0.01 μg/mL NGF-7S.

When the cells had grown for 2 days up to 4 weeks, the experiments were done. Cells were chosen based on size and presence of neurites. Small cells with long processes were used for recording (most likely to be C neurons, with native VR1 receptors).

The cells were recorded with conventional whole cell voltage clamp patch clamp, using the following solutions (calcium ion free):

The extracellular solution comprised (in mM): NaCl 137, KCl 5, $MgCl_2*H_2O$ 1.2, HEPES 10, Glucose 10, EGTA 5, Sucrose 50, pH to 7.4 with NaOH.

The intracellular solution comprised K-gluconate 140, NaCl 3, $MgCl_2*H_2O$ 1.2, HEPES 10, EGTA 1, pH to 7.2 with KOH. When the cells were penetrated with suction, a puff of capsaicin (500 nM) was used to determine if the cell expressed VR1 receptor. If not, a new cell was chosen. If yes, then the compounds were added in increasing doses before the capsaicin pulse (500 nM), to determine an $IC_{50}$ value.

List of Abbreviations
VR1 vanilloid receptor 1
IBS irritable bowel syndrome
IBD inflammatory bowel disease
GERD gastro-esophageal reflux disease
DRG Dorsal Root Ganglion
BSA Bovine Serum Albumin
HEPES 4-(2-Hydroxyethyl)piperazine-1-ethanesulfonic acid
EGTA Ethylene glycol-bis(2-aminoethylether)-N,N,N',N'-tetraacetic acid
DMEM Dulbeccos Modified Eagle's Medium Results Typical $IC_{50}$ values as measured in the assays described above are 150 nM or less. In one aspect of the invention the $IC_{50}$ is below 10 nM

TABLE 3

Specimen results from the hVR1 FLIPR

| Example No. | Name | $IC_{50}$ |
| --- | --- | --- |
| 1 | N-[(1S)-1-(4-isopropoxyphenyl)ethyl]-2-(7-nitro-1H-benzimidazol-1-yl)acetamide | 1 nM |
| 4 | N-((1S)-1-{4-[(1-methylprop-2-yn-1-yl)oxy]phenyl}ethyl)-2-(7-nitro-1H-benzimidazol-1-yl)acetamide | 3 nM |
| 12 | N-{1-[6-(cyclopentyloxy)pyridine-3-yl]ethyl}-2-(7-nitro-1H-benzimidazol-1-yl)acetamide | 5 nM |
| 15 | N-[(1S)-1-(4-{[(1S)-1-methylpropyl]oxy}phenyl)ethyl]-2-(7-nitro-1H-benzimidazol-1-yl)acetamide | 1 nM |
| 16 | N-(1-{4-[chloro(difluoro)methyl]phenyl}ethyl)-2-(7-nitro-1H-benzimidazol-1-yl)acetamide | 10 nM |
| 22 | 2-(7-nitro-1H-benzimidazol-1-yl)-N-{1-[4-(1,1,2,2-tetrafluoroethoxy)phenyl]ethyl}acetamide | 5 nM |
| 36 | 2-(7-nitro-1H-benzimidazol-1-yl)-N-{1-[4-(trifluoromethoxy)phenyl]ethyl}acetamide | 9 nM |
| 37 | 2-(7-nitro-1H-benzimidazol-1-yl)-N-{1-[4-(trifluoromethyl)phenyl]ethyl}acetamide | 6 nM |
| 39 | N-{1-[4-(cyclopentyloxy)-3-fluorophenyl]ethyl}-2-(7-nitro-1H-benzimidazol-1-yl)acetamide | 1 nM |
| 40 | N-[1-(4-cyclopropylphenyl)ethyl]-2-(7-nitro-1H-benzimidazol-1-yl)acetamide | 3 nM |
| 47 | N-{1-[4-{[(2S)-2-Methoxypropyl]oxy}-3-(trifluoromethyl)phenyl]ethyl}-2-(7-nitro-1H-benzimidazol-1-yl)acetamide | 8 nM |
| 48 | N-{1-methyl-2-[3-(trifluoromethyl)phenoxy]ethyl}-2-(7-nitro-1H-benzimidazol-1-yl)acetamide | 7 nM |

TABLE 4

Specimen results from the aqueous solubility test

| Example No. | Name | Aqueous solubility at pH 7.4 |
| --- | --- | --- |
| 3 | N-{(1S)-1-[4-(2-fluoroethoxy)phenyl]ethyl}-2-(7-nitro-1H-benzimidazol-1-yl)acetamide | 90 μM |
| 5 | N-{(1S)-1-[4-(2-methoxy-1-methylethoxy)phenyl]ethyl}-2-(7-nitro-1H-benzimidazol-1-yl)acetamide | 97 μM |
| 6 | N-[(1S)-1-(4-ethoxyphenyl)ethyl]-2-(7-nitro-1H-benzimidazol-1-yl)acetamide | 72 μM |
| 9 | N-{1-[6-(2,2-difluoroethoxy)pyridin-3-yl]ethyl}-2-(7-nitro-1H-benzimidazol-1-yl)acetamide | 98 μM |
| 14 | 2-(7-nitro-1H-benzimidazol-1-yl)-N-{1-[4-(2,2,2-trifluoroethoxy)phenyl]ethyl}acetamide | 63 μM |
| 19 | N-{1-[4-(2,2-difluoroethoxy)phenyl]ethyl}-2-(7-nitro-1H-benzimidazol-1-yl)acetamide | 75 μM |

TABLE 4-continued

Specimen results from the aqueous solubility test

| Example No. | Name | Aqueous solubility at pH 7.4 |
|---|---|---|
| 24 | 2-(7-cyano-1H-benzimidazol-1-yl)-N-(1-{4-[2-fluoro-1-(fluoromethyl)ethoxy]phenyl}ethyl)acetamide | 94 μM |
| 29 | 2-(7-nitro-1H-benzimidazol-1-yl)-N-{1-[5-(trifluoromethyl)pyridin-2-yl]propyl}acetamide | 92 μM |
| 30 | 2-(7-nitro-1H-benzimidazol-1-yl)-N-{1-[5-(trifluoromethyl)pyridin-2-yl]ethyl}acetamide | 97 μM |
| 31 | 2-(7-chloro-1H-benzimidazol-1-yl)-N-{1-[3-chloro-5-(trifluoromethyl)pyridin-2-yl]ethyl}acetamide | 87 μM |
| 32 | N-{1-[3-chloro-5-(trifluoromethyl)pyridin-2-yl]ethyl}-2-(7-nitro-1H-benzimidazol-1-yl)acetamide | 87 μM |
| 35 | 2-(7-chloro-1H-benzimidazol-1-yl)-N-[1-(6-isopropoxypyridin-3-yl)ethyl]acetamide | 100 μM |
| 38 | N-[1-(6-isopropoxypyridin-3-yl)ethyl]-2-(7-nitro-1H-benzimidazol-1-yl)acetamide | 86 μM |
| 41 | N-[1-(4-ethynylphenyl)ethyl]-2-(7-nitro-1H-benzimidazol-1-yl)acetamide | 82 μM |
| 42 | 2-(7-chloro-1H-benzimidazol-1-yl)-N-[1-(4-ethynylphenyl)ethyl]acetamide | 77 μM |
| 46 | N-{1-[4-[(1-Methylpiperidin-4-yl)oxy]-3-(trifluoromethyl)phenyl]ethyl}-2-(7-nitro-1H-benzimidazol-1-yl)acetamide | 100 μM |

Biological Tests

In Vivo Experiments

The in vivo pharmacological properties of some of the compounds according to the present invention have been determined using two classical NSAID-sensitive inflammatory models, the Carrageenan model and the Freund's Complete Adjuvant (FCA) model.

In the former, Carrageenan-lambda (algae-derived polysaccharide, type IV, 100 μl, from Sigma-Aldrich), dissolved in sterile saline 0.9% at a concentration of 1%, and in the latter FCA (25 μl, from Sigma-Aldrich, (1 ml of FCA contains 1 mg mycobacterium tuberculosis heat killed and dried, 0.85 ml mineral oil and 0.15 ml mannide monooleate, cf. Nagakura et al. in *Journal of Pharmacology and Experimental Therapeutics*, 2003; 306(2):490-497)) is injected into the subcutaneous space under the plantar surface (intra-plantar; i.pl.) of the rat left hind paw. This creates an inflammatory response, with accompanying edema, redness, and hyperalgesia. Heat (and mechanical) hyperalgesia is fully developed by 3 hours for carrageenan, and remains stable for 6 hours, while FCA is fully developed by 24 h and remains stable for weeks. In order to assess the degree of hyperalgesia, the heat plantar test was chosen, as it is a robust, consistent, and reproducible endpoint (based on the Hargreaves method of assessing nociception, cf. *Pain*, 1988; 32(1):77-88). Rats are placed in individual plexiglass boxes on a glass surface, which is maintained at 30° C., and a heat-source (rate of heat increase: ~1.1° C./s) is focused onto the plantar surface of the affected paw. The time from the initiation of the heat until the animal withdraws the paw is recorded. A decrease in Paw Withdrawal Latency (PWL) relative to naïve animals indicates a hyperalgesic state.

The degree of reversal of hyperalgesia is measured by the ability of the compounds to return PWL to normal levels. N-[(1S)-1-(4-tert-butylphenyl)ethyl]-2-(6,7-difluoro-1H-benzimidazol-1-yl)acetamide from Example 52, the more active enantiomer of 2-(7-Nitro-benzoimidazol-1-yl)-N-{1-[6-(2,2,3,3-tetrafluoro-propoxy)-pyridin-3-yl]-ethyl}-acetamide from Example 10, and N-{(S)-1-[4-(2-Fluoro-1-fluoromethyl-ethoxy)-phenyl]-ethyl}-2-(7-nitro-benzoimidazol-1-yl)-acetamide from Example 2 were orally administered (the more active enantiomer of 2-(7-Nitro-benzoimidazol-1-yl)-N-{1-[6-(2,2,2-trifluoro-ethoxy)-pyridin-3-yl]-ethyl}-acetamide from Example 7 was given by subcutaneous injection) during the established phase of inflammation and tested at their respective Tmax. Said more active enantiomers were obtained by preparing the compounds from intermediates that had been resolved enzymatically and coupled to the acids to produce target compounds having ~90% enantiopurity. The latter were additionally purified by means of chiral chromatography. The PWL of each animal is measured twice, and the average of the two is taken as the response. The responses of all animals within a given group are then averaged, and Standard Deviation and Standard Error of the Mean (SEM) are calculated for each group. The data is expressed as mean±SEM. Statistical significance is assessed with a T-test for comparison between naïve and treated groups, and One Way ANOVA followed by Holm-Sidak multiple comparisons versus control (vehicle) group test for drug effectiveness. The level of statistical significance is set at $p<0.05$. GraphPad Prism® version 4 is used for non-linear regression analysis (using the variable slope sigmoidal equation model) of raw data to calculate the ED50, EC50, EC80, and Emax.

Prior to any manipulation, rats (150-175 g, Charles River, St. Constant, Canada) were housed in groups of 7-9 in a temperature controlled room (22±1.5° C., 30-80% humidity, 12 h light/dark cycle) and were acclimatized in the animal facility for at least one day prior to use. All experimental protocols are approved by the AstraZeneca Animal Care Committee. Experiments are performed during the light phase of the cycle, rooms are illuminated at 300 lux intensity. Animals have food and water ad libitum.

In vivo efficacy and potency of the tested compounds in nociceptive pain are summarized in Table 5 below. The tested compounds are potent and effective in reversing both carrageenan- and FCA-induced heat hyperalgesia.

TABLE 5

Efficacy and Potency of tested compounds in the carrageenan and FCA models in vivo

| Compound from Example # | Carrageenan model | | | | FCA model |
|---|---|---|---|---|---|
| | 52 | 10 active enantiomer | 2 | 7 active enantiomer | 52 |
| ED50 ($\mu$mol/kg) | 37.4 | 3.2 | 1.3 | 6.0 | 119.7 |
| EC50 ($\mu$M) | 0.5 | 0.39 | 0.105 | 0.75 | 1.6 |
| Emax observed (%) | 74 | 81 | 79 | 94 | 78 |
| Extrapolated Emax (%) | >100 | >100 | 79 | >100 | >100 |
| EC80 ($\mu$M) | 1.4 | 2.1 | 0.17 | 2.0 | 4.6 |

The invention claimed is:

1. The compound N-[(1S)-1-(4-tert-butylphenyl)ethyl]-2-(6,7-difluoro-1H-benzimidazol-1-yl)acetamide or a pharmaceutically acceptable salt thereof.

2. A pharmaceutical composition comprising a compound or a pharmaceutically acceptable salt thereof according to claim 1 in association with one or more pharmaceutically acceptable diluents, excipients and/or inert carriers.

3. A method of treating acute pain in a human which comprises administering to a person in need thereof an effective amount of a compound or a pharmaceutically acceptable salt thereof according to claim 1.

4. A method of treating chronic pain in a human which comprises administering to a person in need thereof an effective amount of a compound or a pharmaceutically acceptable salt thereof according to claim 1.

5. A method of treating acute neuropathic pain in a human which comprises administering to a person in need thereof an effective amount of a compound or a pharmaceutically acceptable salt thereof according to claim 1.

6. A method of treating chronic neuropathic pain in a human which comprises administering to a person in need thereof an effective amount of a compound or a pharmaceutically acceptable salt thereof according to claim 1.

7. A method of treating acute and chronic inflammatory pain in a human which comprises administering to a person in need thereof an effective amount of a compound or a pharmaceutically acceptable salt thereof according to claim 1.

8. A method of treating acute nociceptive pain in a human which comprises administering to a person in need thereof an effective amount of a compound or a pharmaceutically acceptable salt thereof according to claim 1.

9. A method of treating chronic nociceptive pain in a human which comprises administering to a person in need thereof an effective amount of a compound or a pharmaceutically acceptable salt thereof according to claim 1.

10. A method of treating migraine in a human which comprises administering to a person in need thereof an effective amount of a compound or a pharmaceutically acceptable salt thereof according to claim 1.

* * * * *